(12) United States Patent
Nathan et al.

(10) Patent No.: US 11,141,314 B2
(45) Date of Patent: Oct. 12, 2021

(54) BIOABSORBABLE TISSUE SUPPORT ADJUNCTIVE TO TISSUE PIERCING

(71) Applicant: BIOPIERCE CANADA LTD., Souris (CA)

(72) Inventors: Mark David Nathan, Sioux Falls, SC (US); Michaella Maxine Silber, Port Washington, NY (US); Norman Isaac Silber, Port Washington, NY (US); Ali Ahmadi, Cornwall (CA); Emad Naseri, Charlottetown (CA)

(73) Assignee: BIOPIERCE TECHNOLOGIES, LLC, Souris (CA)

( * ) Notice: Subject to any disclaimer, the term of this patent is extended or adjusted under 35 U.S.C. 154(b) by 75 days.

(21) Appl. No.: 16/778,467

(22) Filed: Jan. 31, 2020

(65) Prior Publication Data

US 2020/0163799 A1 May 28, 2020

Related U.S. Application Data

(63) Continuation-in-part of application No. 15/307,847, filed as application No. PCT/US2015/030699 on May 14, 2015, now Pat. No. 10,548,775.
(Continued)

(51) Int. Cl.
*A61F 11/00* (2006.01)
*A44C 7/00* (2006.01)
*A61M 31/00* (2006.01)

(52) U.S. Cl.
CPC .............. *A61F 11/00* (2013.01); *A44C 7/001* (2013.01); *A61F 2210/0004* (2013.01);
(Continued)

(58) Field of Classification Search
CPC ..... A61L 31/148; A61L 31/16; A01K 11/001; A61F 11/00; A61F 2210/0004;
(Continued)

(56) References Cited

U.S. PATENT DOCUMENTS

| 6,306,170 B2 | 10/2001 | Ray | A61F 2/446 606/246 |
|---|---|---|---|
| 2005/0027315 A1 | 7/2005 | Plateroti | |

(Continued)

*Primary Examiner* — Mohamed G Gabr

(57) ABSTRACT

A bioabsorbable tissue support is inserted into a tissue of a subject during, or after, puncture of the tissue. The bioabsorbable tissue support includes a material that is gradually absorbed into the punctured tissue in time, and disappears. The bioabsorbable tissue support may be inserted standing alone, or in association with a permanent or temporary non-bioabsorbable tissue support, may define the shape of the punctured hole, and/or may release useful or ornamental chemicals into the punctured tissue. The chemical may include an antibacterial material, an antifungal material, an antimicrobial material, topical anesthetic, a temporary or permanent dye material, and/or an antiproliferative agent. The non-bioabsorbable tissue support may include a self-expanding material that enlarges the size of the puncture in time. The bioabsorbable tissue support may have the form of a tube and/or a mesh of variable peripheral shapes, be elongated, and/or have attachable and detachable end plates and pointed tips.

24 Claims, 16 Drawing Sheets

Related U.S. Application Data

(60) Provisional application No. 61/993,363, filed on May 15, 2014.

(52) U.S. Cl.
CPC . *A61F 2240/001* (2013.01); *A61F 2250/0003* (2013.01); *A61F 2250/0067* (2013.01); *A61M 31/002* (2013.01); *A61M 2205/04* (2013.01); *A61M 2210/0662* (2013.01)

(58) Field of Classification Search
CPC ...... A61F 2250/0003; A61F 2250/0031; A61F 2250/0067
See application file for complete search history.

(56) References Cited

U.S. PATENT DOCUMENTS

| | | | | |
|---|---|---|---|---|
| 2005/0191331 | A1 | 9/2005 | Hunter | A61B 17/11 424/423 |
| 2006/0276841 | A1 | 12/2006 | Barbieri | A61B 17/0401 606/232 |
| 2008/0221533 | A1* | 9/2008 | Matityahu | A44C 15/0095 604/290 |
| 2013/0006289 | A1* | 1/2013 | Harper | A44C 7/001 606/188 |
| 2014/0067063 | A1 | 3/2014 | Bonutti | A61F 2/441 623/13.15 |

\* cited by examiner

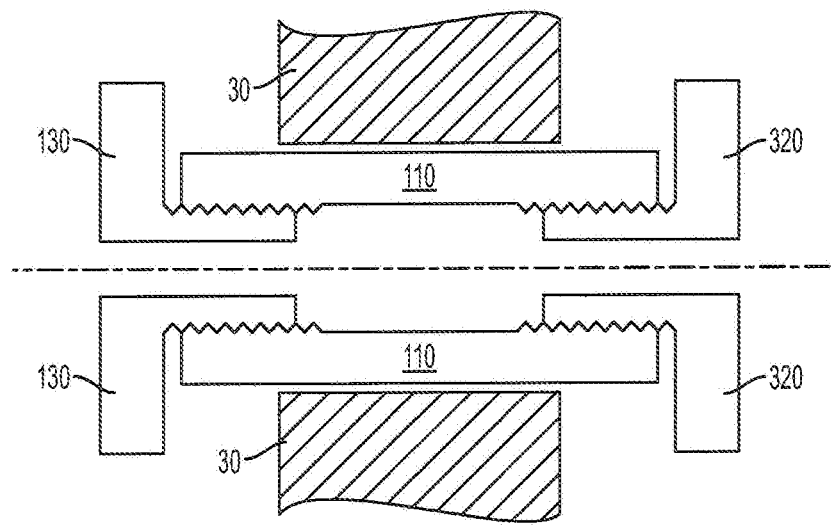
FIG. 2E
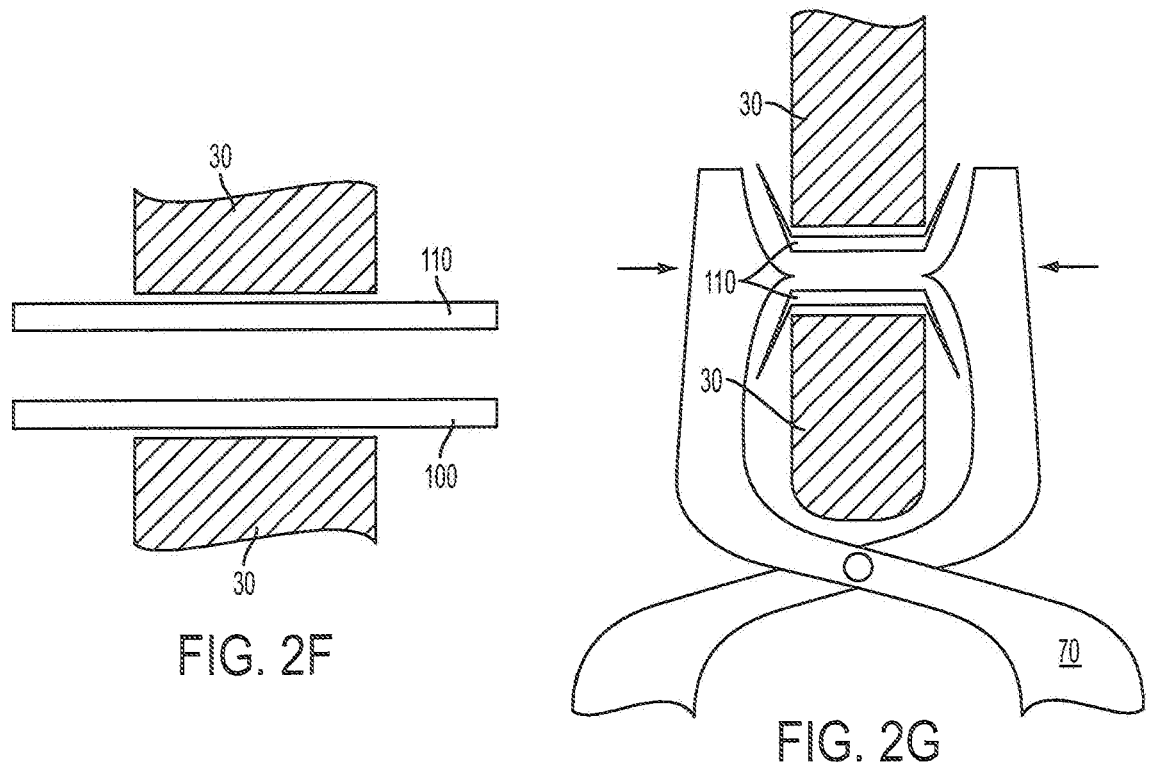
FIG. 2F
FIG. 2G

BIOABSORBABLE TISSUE SUPPORT ADJUNCTIVE TO TISSUE PIERCING

CROSS REFERENCE TO RELATED APPLICATIONS

This application is a continuation-in-part of U.S. patent application Ser. No. 15/307,847, filed Oct. 31, 2016, which is a 371 U.S. National Stage Application of PCT/US2015/30699 filed on May 14, 2015, which claims the benefit of U.S. Provisional Application No. 61/993,363, filed May 15, 2014, the entire contents of which are incorporated herein by reference.

BACKGROUND

The present invention relates to a device including a bioabsorbable tissue support adjunctive to tissue piercing and a method of using the same.

Tissue piercing, including the piercing of cartilage and skin, has been employed both for humans and other lifeforms for various purposes. For example, ear piercing is performed among the general population to enable attachment of ornamental earrings. Tissue piercing for animals for identification purposes, therapeutic purposes, and/or ornamental purposes is also widely practiced.

Tissue piercing is inherently an unsafe procedure because tissue piercing inevitably exposes portions of tissues that are not exposed to the ambient in normal conditions. Exposure of cut tissues to the ambient can trigger exposure to bacteria and/or viruses, and in some cases, may cause severe inflammation that cause deformation of the pierced tissues and/or life-threatening medical conditions.

Thus, methods and devices for safely performing tissue piercing for humans and/or other lifeforms are desirable.

SUMMARY

A bioabsorbable tissue support is inserted into a tissue of a subject during, or after, puncture of the tissue. The bioabsorbable tissue support includes a material that is gradually absorbed into the punctured tissue in time, and disappears. The bioabsorbable tissue support may be inserted standing alone, or in association with a permanent or temporary non-bioabsorbable tissue support. The bioabsorbable tissue support may define the shape of the punctured hole, and/or may release useful or ornamental chemicals into the punctured tissue. The chemical may include an antibacterial material, an antifungal material, an antimicrobial material, topical anesthetic, a temporary or permanent dye material, and/or an antiproliferative agent. The non-bioabsorbable tissue support may include a self-expanding material that enlarges the size of the puncture in time. The bioabsorbable tissue support may be in the form of a tube and/or a mesh which may be expandable or expanding, and may be elongated and/or may have an attachable or detachable endplate and/or pointed tip.

According to an aspect of the present disclosure, a device including a bioabsorbable tissue support is provided. The bioabsorbable tissue support contains at least one bioabsorbable material, includes an elongated portion having a uniform or tapered cross-sectional shape and is configured to contact an inner surface of a puncture in a tissue, and has a rigidity to maintain an original shape until the at least one bioabsorbable material is absorbed into a body of a subject to which the device is inserted. Each of the at least one bioabsorbable material is selected from a group consisting of therapeutic medical chemicals, anesthetic materials, dye materials, and antiproliferative agents.

In one embodiment, a cavity extends through the elongated portion, and the elongated portion has a tubular shape.

In another embodiment, the bioabsorbable tissue support further contains a pointed tip portion attached to, and/or located at, one end of the elongated portion. The bioabsorbable tissue support can further include an end plate that is attached to one or both ends of the elongated portion and extending further outward from an axis passing through a center of mass of the elongated portion in a lengthwise direction of the elongated portion than a maximum lateral dimension of the cross-sectional shape of the elongated portion.

In even another embodiment, the elongated portion has a tubular mesh structure with openings therein.

In yet another embodiment, the uniform or tapered cross-sectional shape has a non-circular periphery.

In still another embodiment, the at least one bioabsorbable material includes a plurality of layers having different compositions. The plurality of layers can include at least an outer layer having a first composition having a first bioabsorption half-life, and an inner layer surrounded by the outer layer and having a second composition having a second bioabsorption half-life that is longer than the first bioabsorption half-life. Additionally or alternatively, the plurality of layers can include a first layer providing a first functionality selected from therapeutic treatment of the puncture, anesthetic treatment of the puncture, coloring of a region around the puncture, and prevention of change of shape of the puncture; and a second layer providing a second functionality selected therapeutic treatment of the puncture, anesthetic treatment of the puncture, coloring of a region around the puncture, and prevention of change of shape of the puncture, the second functionality being different from the first functionality.

In still yet another embodiment, the device can further include an expansion-inducing device embedded within a cavity in the elongated portion. The expansion-inducing device may be a balloon, which can include a tube fitting portion configured to receive an end portion of a tube, which may be configured to provide a fluid therethrough for expansion of the balloon. The expansion inducing device may also be an expandable mold or structure or form with a noncircular periphery to expand the tissue support into a noncircular form.

In further another embodiment, the device consists of the bioabsorbable tissue support. In even further another embodiment, the device further includes a non-bioabsorbable tissue support embedded within the bioabsorbable tissue support. At least a portion of the bioabsorbable tissue support is located outside of said non-bioabsorbable tissue support. In one case, the portion of the tissue support can receive end plates, rivets, or ornamental adornments by threading, snap, pressure and/or other means.

In one case, the tissue support includes at least two components, the bioabsorbable tissue support and the non-bioabsorbable issue support, and the non-bioabsorbable tissue support includes an elastic material that is spring loaded in a compressed state by the bioabsorbable tissue support, and is configured to expand during bioabsorption of the bioabsorbable tissue support and to conform to a target shape upon release of stress in the elastic material. In one case, the non-bioabsorbable tissue support can be composed of a material that swells or expands to conform to a target shape when expanded by pressure, or activated by contact with water or a chemical compound, or by gradual absorption of the bioabsorbable tissue support.

In another case, the non-bioabsorbable tissue support includes a metallic material or a ceramic material that maintains an original shape after the bioabsorbable tissue support is absorbed by the tissue.

The non-bioabsorbable tissue can include a sidewall surface including an opening and a hanging structure affixed to an end of the sidewall surface, the hanging structure being selected from a hook, a hoop for hanging a hook, a hole in a plate, and an elastic clip.

In yet further another embodiment, the bioabsorbable tissue support includes a bioabsorbable dye, and/or at least one material selected from the group consisting of therapeutic medical chemicals, anesthetic materials, and antiproliferative agents.

According to another aspect of the present disclosure, a method of operating a device is provided. A device including a bioabsorbable tissue support is provided. The bioabsorbable tissue support contains at least one bioabsorbable material, includes an elongated portion having a uniform or tapered cross-sectional shape and configured to contact an inner surface of a puncture in a tissue, and has a rigidity to maintain an original shape until the at least one bioabsorbable material is absorbed into a body of a subject to which the device is inserted. Each of the at least one bioabsorbable material is selected from a group consisting of therapeutic medical chemicals, anesthetic materials, dye materials, and antiproliferative agents. A through-hole is formed through a tissue portion of a lifeform. The device is inserted through the through-hole simultaneously with, or after, formation of the through-hole.

In one embodiment, the bioabsorbable tissue support further contains a pointed tip portion attached to, or located at, one end of the elongated portion. The method further includes detaching the pointed tip from the elongated portion after insertion of the device.

In another embodiment, the elongated portion can be inflated by providing a balloon within a cavity in the elongated portion; and outwardly expanding the elongated portion by inflating the balloon.

According to another aspect, there is provided a device for support of a puncture in a tissue, said device comprising: a bioabsorbable tissue support comprising: an tubular elongated sleeve having a cross-sectional shape and a thickness defined between an inner surface and an outer surface of the tubular elongated sleeve, wherein the tubular elongated sleeve is configured to contact an inner surface of said puncture; and a cavity extending through said elongated sleeve for receiving an earring or an identification device; wherein the tubular elongated sleeve is uniformly made from at least one bioabsorbable material throughout the entire thickness of the tubular elongated sleeve, the bioabsorbable material comprising a polymer; wherein the tubular elongated sleeve is configured to extend through the tissue and remains after said at least one bioabsorbable material is absorbed through at least a skin of a subject; wherein one or more of said at least one bioabsorbable material comprises a functional compound mixed within the polymer for absorption through the skin as the bioabsorbable material is absorbed, the functional compound selected from a group consisting of therapeutic medical chemicals, anesthetic materials, dye materials, and antiproliferative agents.

In one embodiment, the identification device is an RFID tag. In one embodiment, the bioabsorbable tissue support comprises a removable stud, wherein the stud comprises: a rod portion for insertion into the cavity, the rod having a first end and a second end; the pointed tip disposed at the first end of the rod portion, such that the bioabsorbable tissue support is configured to pierce through the tissue for creating the puncture; and a flange proximate to the first end and configured to abut against a first end of the tubular elongated sleeve when the stud is inserted into the cavity, thereby keeping the pointed tip exposed out of the tubular elongated sleeve. In one embodiment, the bioabsorbable tissue support comprises a capping nut configured to removably attach to a second end of the rod portion of the stud, wherein the capping nut has a cross-section that is greater than the cavity, such that when the stud is inserted into the cavity and the capping nut is attached to the second end of the rod portion, the tubular elongated sleeve is secured between the capping nut and the flange potion. In one embodiment, the capping nut is removably attachable to the second end of the rod portion of the stud by threading, snap fit, or pressure fit. In one embodiment, the stud and the capping nut is made of a resin. In one embodiment, the polymer comprises a polylactic-co-glycolic acid (PLGA) polymer matrix. In one embodiment, the tubular elongated sleeve comprises one or more layers having: a first layer comprising a first bioabsorbable material providing a first functionality selected from therapeutic treatment of said puncture, anesthetic treatment of said puncture, coloring of a region around said puncture, and prevention of change of shape of said puncture. In one embodiment, the resin is an UV sensitive resin, and the stud is manufactured by 3D printing. In one embodiment, the first bioabsorbable material comprises a photopolymer, and the outer layer is manufactured by 3D printing. In one embodiment, the stud has a first cross-sectional shape, and wherein the stud has a higher rigidity than the tubular elongated sleeve thereby reinforcing a second cross-sectional shape of the tubular elongated sleeve. In one embodiment, the tubular elongated sleeve comprises a second layer comprising a second bioabsorbable material providing a second functionality selected from therapeutic treatment of said puncture, anesthetic treatment of said puncture, coloring of a region around said puncture, and prevention of change of shape of said puncture, said second functionality being different from said first functionality. In one embodiment, the first bioabsorbable material has a first absorption half-life, and the second bioabsorbable material has a second bioabsorption half-life that is longer than said first bioabsorption half-life. In one embodiment, the functional compound is microencapsulated. In one embodiment, the elongated sleeve has a tubular mesh structure with openings therein. In one embodiment, the device further comprises an expansion-inducing device embedded within a cavity in said elongated sleeve. In one embodiment, the non-bioabsorbable tissue support includes an elastic material that is spring loaded in a compressed state by said bioabsorbable tissue support, and is configured to expand during bioabsorption of said bioabsorbable tissue support and to conform to a target shape upon release of stress in said elastic material. In one embodiment, the expansion-inducing device is a balloon, a spring, or a coil. In one embodiment, the bioabsorbable tissue support includes: a bioabsorbable dye; and at least one material selected from the group consisting of therapeutic medical chemicals, anesthetic materials, and antiproliferative agents. In one embodiment, the PLGA polymer matrix has a lactic to glycolic ratio of between 15:85 to 85:15. In one embodiment, the PLGA polymer matrix has a molecular weight of greater than 100 kDa. In one embodiment, the pointed tip is removably attached to the second end of the rod portion of the stud by threading, snap fit, or pressure fit. In one embodiment, one or both of the first end and the second end of the rod is configured for removable attachment to the earring or the identification device. In one embodiment, the thickness of the tubular elongated sleeve is between 10 micro meter to 1000 micro meter.

BRIEF DESCRIPTION OF THE DRAWINGS

FIG. 2E is an illustration of a configuration in which an end plate and a plug plate are attached to an elongated portion.

FIG. 2F is an illustration of a configuration for forming flattened end plates after insertion of the first exemplary device and prior to crimping.

FIG. 2G is an illustration of the configuration in which flattened end plates have been formed.

DETAILED DESCRIPTION

Figure 1A:
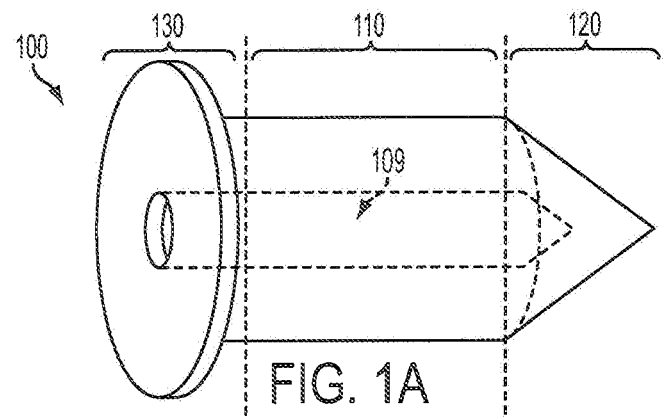
FIG. 1A is an angled view of a first exemplary device including a bioabsorbable tissue support that incudes an end plate and a pointed tip.

As stated above, the present invention relates to a device including a bioabsorbable tissue support for tissue piercing and a method of using the same. These aspects of the present disclosure are now described in detail with accompanying figures. It is noted that like reference numerals refer to like elements across different embodiments. The drawings are not necessarily drawn to scale. As used herein, ordinals such as "first" and "second" are employed merely to distinguish similar elements, and different ordinals may be employed to designate a same element in the specification and/or claims.

As used herein, a "lifeform" refers to all biologically living beings, and includes, among others, animals, including domesticated, farm, and wild animals, research animals, and plants. Humans are included among animals for the purposes of this disclosure.

As used herein, a "bioabsorbable" material refers to a material that is absorbed by at least one lifeform. A "bioabsorbable" element refers to an element that includes at least one bioabsorbable material. A bioabsorbable material may be a material that is absorbed by tissue cells of at least one animal, and/or may be a material that is absorbed by tissue cells of at least one plant, and/or may be a material that is absorbed by human tissue cells. A bioabsorbable material may be a material that is absorbed into an animal through animal skin. A bioabsorbable material may be a material that is absorbed into humans through human skin.

As used herein, a "non-bioabsorbable" material refers to a material that is not a bioabsorbable material.

As uses herein, a "tissue" refers to a cell or a group of cells of a lifeform.

As used herein, a "tissue support" refers to a structure designed to provide a structural support to a tissue.

As used herein, a "bioabsorbable tissue support" refers to a tissue support containing at least one bioabsorbable material, and may consist of the at least one bioabsorbable material, may composed primarily of the at least one bioabsorbable material, or may include a non-bioabsorbable material.

An element is "composed primarily of" a material if the mass of the material is more than 50% of the total mass of the element.

As used herein, a "subject" refers to a lifeform to which a device including a bioabsorbable tissue support is applied or attached. A subject includes humans and animals, such as farm animals and pets.

As used herein, a "uniform cross-sectional shape" refers to a cross-sectional shape that is invariant under translation along the direction perpendicular to the plane including the cross-sectional shape.

As used herein, an element is "configured to" perform an action if the element possesses all geometrical features and required mechanical characteristics to perform the action as inherent characteristics of the elements.

As used herein, a "tapered cross-sectional shape" refers to a cross-sectional shape that changes under translation defined along the direction perpendicular to the plane including the cross-sectional shape in such a way that a new cross-sectional shape at a translated location is obtained by expansion or shrinkage of the original cross-sectional shape before translation, and the selection of the direction of translation with respect to the location of the original cross-sectional shape uniquely determines whether a magnification or a reduction is needed to determine the new cross-sectional shape after translation irrespective of the selection of the location of the original cross-sectional shape.

As used herein, a "therapeutic medical chemical" refers to a chemical known in the field of medicine to have a therapeutic effect on humans or animals.

As used herein, an "anesthetic material" refers to a material known in the field of medicine to have anesthetic effect on humans or animals.

As used herein, a "dye material" refers to a material that provides local coloring of a tissue to which it is applied.

As used herein, an "antiproliferative agent" refers to an immunosuppressive material, i.e., a material that blocks or suppresses the proliferative phase of acute cellular rejection, and/or prevents re-growth of tissue or that otherwise would occlude the through-hole.

As used herein, a "bioabsorption half-life" is a time period during which the first one half of the original amount of a topically applied bioabsorbable material is absorbed.

As used herein, an "earring" refers to any object, whether decorative or functional, that is worn directly or indirectly on a subject, such as the ear of a subject. An earring can also be worn on other parts of a subject where a piercing is provided. In embodiments where the subject is a human, an earring is worn in piercings of, for example, navels, cheeks, noses, eyebrows, or genitals. In embodiments where the subject is an animal, an earring is worn in piercings of, for example, the neck, dorsal midline between the shoulder blades, abdomen, ears, thighs, wings, feathers, or webs. Example earrings include, but are not limited to, jewelry or ornamental earrings, identifier earrings (such as colour coded, or engraved earrings), and identifier devices for attachment to a subject.

As used herein, an "identification device" is a device containing or storing identification data, such as encoded identification data, for the purpose of identifying the subject wearing the identification device. Examples of an identification device includes, but are not limited to information tags (having for example, a bar code imprinted thereon), ID chips (such as RFID chips), electronic devices, transmitter, or GPS tracking device.

Figure 1B:
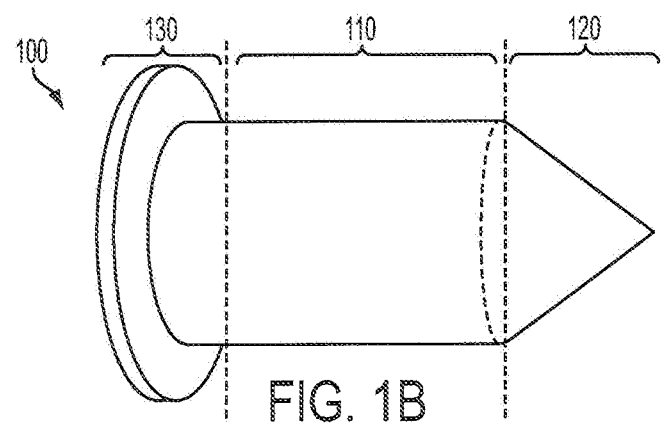
FIG. 1B is another angled view of the first exemplary device including a bioabsorbable tissue support of FIG. 1A.
Figure 1C:
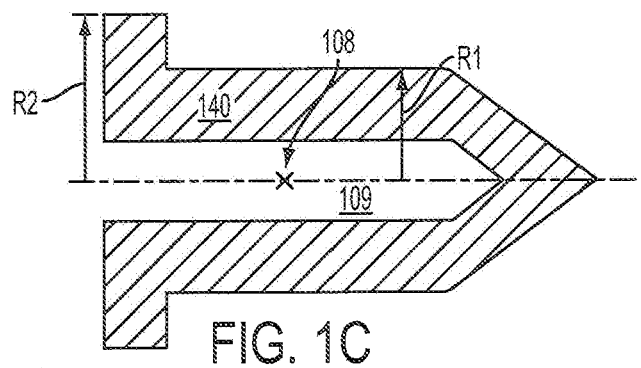
FIG. 1C is a vertical cross-sectional view of the first exemplary device of FIGS. 1A and 1B along a vertical plane containing a lengthwise axis of an elongated portion.

Referring to FIGS. 1A, 1B, and 1C, a first exemplary device 100 includes a bioabsorbable tissue support (110, 120, 130). The bioabsorbable tissue support (110, 120, 130) includes an elongated portion 110, and optionally includes a pointed tip portion 120. The pointed tip potion 120, if present, is attached to an end of the elongated portion 110. In addition, the bioabsorbable tissue support (110, 120, 130) can optionally include an end plate 130. The end plate 130, if present, is attached to another end of the elongated portion 110 that is located on the opposite side of the pointed tip portion 120 (if present). The end plate is integral with, and/or attached to, the elongated portion 110, and if it is attached it may be by threading, snap, pressure and/or other means.

The elongated portion 110 has a uniform or tapered cross-sectional shape. In one embodiment, the elongated portion 110 can have a uniform cross-sectional shape. The outer surface(s) of the elongated portion 110 is/are configured to contact an inner surface of a puncture in a tissue of a subject. Further, the elongated portion 110 has a rigidity that is sufficient to maintain an original shape until the at least one bioabsorbable material is absorbed into the body of the subject to which the first exemplary device 100 is inserted. Optionally, the elongated portion 110 can be non-elastic deformable material, i.e., a plastic material, which can be deformed through pressure and can maintain the deformed shape after deformation.

The dimensions of the elongated portion 110 depend on the lateral dimensions and the thickness of the tissue through which the elongated portion 110 is inserted. For example, for the purpose of ear piercing on humans, the length of the elongated portion 110 can be in a range from 0.3 mm to 1 cm, although lesser and greater lengths can also be employed, and the maximum lateral dimension (e.g., the outer diameter if the elongated portion 110 has a cylindrical shape) can be in a range from 1 mm to 1 cm, although lesser and greater lateral dimensions can also be employed. The dimensions of the elongated portion 110 can be scaled up or down depending on the size of the puncture to be formed within a tissue of a subject.

The direction along which the elongated portion 110 extends is herein referred to as the lengthwise direction of the elongated portion 110. If the elongated portion 110 has a uniform cross-sectional shape, the cross-sectional shape of the elongated portion is invariant under translation along the lengthwise direction of the elongated portion 110. If the elongated portion 110 has a tapered cross-sectional shape, the cross-sectional shape of the elongated portion 110 expands, or shrinks, monotonically with translation along the lengthwise direction of the elongated portion 110. The lengthwise direction that passes through the center of mass 108 of the elongated portion 110 is herein referred to as the "lengthwise axis" of the bioabsorbable tissue support (110, 120, 130). The lengthwise axis passes through the center of mass of the elongated portion 110 in the lengthwise direction of the elongated portion 110.

The elongated portion 110 includes a cavity 109 therein. The cavity 109 can have a uniform cross-sectional shape or a tapered cross-sectional shape. The cross-sectional area of the cavity 109 can be selected to enable passage of a pin or of an attachment (not shown) therethrough. The attachment is the structure that is permanently or temporarily mounted to the subject employing the puncture in the tissue, and can be, for example, an earring for humans, an identification tag for animals, or any other structure that can be attached to the subject. The cavity 109 extends through the elongated portion 110. In one embodiment, the elongated portion 110 can have a tubular shape.

The pointed tip portion 120 has a tapered cross-sectional shape that converges at a pointed tip. If the slope of the pointed tip portion 120 between the elongated portion 110 and the pointed tip may be constant, or may have a non-zero curvature for the shape of the edges in a cross-sectional view along a plane passing through the lengthwise axis of the bioabsorbable tissue support (110, 120, 130). The distal region of the pointed tip portion 120, i.e., the region of the pointed tip portion 120, may have a uniform taper that terminates at a single point, may have a convex dome, or may have a tip having a more acute taper angle than a proximal region of the pointed tip portion 120, i.e., the region of the pointed tip portion 120 adjoined to the elongated portion 110.

The end plate 130 can extend along the direction of a plane perpendicular to the lengthwise direction of the elongated portion 110. The end plate 130 has an opening in the middle such that the opening of the end plate 130 is connected to the cavity 109 within the elongated portion. In one embodiment, the opening in the end plate 130 and the portion of the cavity 109 that adjoins the opening of the end plate can have the same cross-sectional shape.

The end plate 130 can be attached to the end of the elongated portion 110 that is the most distal from the pointed tip portion 120. The end plate 130 can extend further outward from the lengthwise axis than the maximum lateral dimension of the cross-sectional shape of the elongated portion 110. It is understood that the maximum lateral dimension of the cross-sectional shape of the elongated portion 110 is the maximum distance between points in the elongated portion 110 and the lengthwise axis. In an illustrative example, if the elongated portion 110 and the end plate 130 are cylindrical, the maximum lateral dimension of the elongated portion 110 can be a first radius R1 and the maximum lateral dimension of the end plate 130 can be a second radius R2 that is greater than the first radius R1.

In one embodiment, the end plate 130 can have a uniform thickness throughout. In one embodiment, the end plate 130 can have a circular outer periphery, an elliptical outer periphery, a superelliptical outer periphery, a polygonal outer periphery, or a curvilinear outer periphery of an arbitrary closed curve. In one embodiment, the end plate 130 can have a shape of a circular inner periphery, an elliptical inner periphery, a superelliptical inner periphery, a polygonal inner periphery, or a curvilinear inner periphery of an arbitrary closed curve. In one embodiment, the outer periphery can be spaced from the inner periphery at all azimuthal angles around an axis that passes through the elongated portion 110 along the lengthwise direction of the elongated portion 110.

The bioabsorbable tissue support (110, 120, 130) contains at least one bioabsorbable material. In one embodiment, the bioabsorbable tissue support (110, 120, 130) can consist of the at least one bioabsorbable material.

In another embodiment, the bioabsorbable tissue support (110, 120, 130) can be composed primarily of the at least one bioabsorbable material and include a non-bioabsorbable material. If present, the non-bioabsorbable material can be a dye material, metallic particulates, a polymer material that slowly polymerizes upon exposure to air, air embedded in micropores, a matrix material such as Vaseline, or combinations thereof. The mass percentage of the non-bioabsorbable material within the bioabsorbable tissue support (110, 120, 130), if present, can be within a range of 0.01 parts per billion (p.p.b.) to less than 50%.

In one embodiment, the bioabsorbable tissue support (110, 120, 130) is composed primarily of the at least one bioabsorbable material and include at least a non-bioabsorbable material comprising an identification device. In one embodiment, the identification device is an tag for animal tagging. In one embodiment, the identification device is an RFID chip for animal tagging.

Each of the at least one bioabsorbable material can have a functionality. The types of functionalities that a bioabsorbable material can have include, but are not limited to, therapeutic treatment of the puncture, anesthetic treatment of the puncture, coloring of a region around the puncture, and prevention of change of shape of the puncture. Each of the at least one bioabsorbable material can be selected from a group including, and not limited to, therapeutic medical chemicals, anesthetic materials, dye materials, and antiproliferative agents. In one embodiment, each of the at least one bioabsorbable material can be selected from a group consisting of therapeutic medical chemicals, anesthetic materials, dye materials, and antiproliferative agents.

If therapeutic treatment of the puncture is desired, the at least one bioabsorbable material can include one or more of antibacterial materials, antifungal materials, antimicrobial materials, or other medical chemicals known to be absorbable into tissues and to provide desired therapeutic effects. In some embodiments, the antibacterial materials, antifungal materials, antimicrobial materials, or other medical chemicals are evenly dispersed throughout the bioabsorbable tissue support. In other embodiments, the antibacterial materials, antifungal materials, antimicrobial materials, or other medical chemicals are provided in one or more layers of the bioabsorbable tissue support. In alternate embodiments, the antibacterial materials, antifungal materials, antimicrobial materials, or other medical chemicals are encapsulated or microencapsulated, and dispersed in the bioabsorbable tissue support either uniformly or dispersed in one or more layers of the bioabsorbable tissue support.

In one embodiment, the bioabsorbable material can be in the form of a mixture between a functional material and a polymer matrix material. The polymer matrix material includes, for example, poly-L-lactic acid, polyglycolic acid, poly(D-L-kactide/plycolide) copolymer, polycaprolactone, other bioabsorbable hydrocarbon-based polymers, and/or a bioabsorbable metallic material known to be absorbable through tissue such as a magnesium alloy or a zinc alloy employed in coronary stents. The functional material can include therapeutic medical chemicals, anesthetic materials, dye materials, and antiproliferative agents. In one embodiment, a plurality of materials having different types of functionalities may be present within the bioabsorbable tissue support (110, 120, 130) either in layered structures having different compositions, or in a single composition having multiple functional components.

In preferred embodiments, polymer matrix material comprises lactic acid and glycolic acid, and the bioabsorbable tissue support is fabricated from poly-lactic-co-glycolic acid (PLGA) constructs. In some embodiments, solvents such as methyl ethyl ketone (MEK) is used make the polymer matrix material from lactic acid and glycolic acid. In some embodiments, the concentration of PLGA in the solvent to make a PLGA polymer is between 60-120% w/v. In one embodiment, the concentration of PLGA in the solvent is 60%, 70%, 80%, 90%, 100%, 110%, or 120%.

The present inventors have discovered that specific ratios of lactic acid to glycolic acid allows for a polymer matrix material that has sufficient rigidity to puncture through a tissue and/or maintain the original shape of the puncture until the bioabsorbable material is absorbed into a body of a subject to which the bioabsorbable tissue support is inserted.

In one embodiment, the lactic to glycolic ratio of the PLGA polymer is between 15:85 to 85:15. In one embodiment, the lactic to glycolic ratio of the PLGA polymer is 15:85, 20:80, 30:70, 40:60, 50:50, 60:40, 70:30, 80:20, or 85:15.

In one embodiment, the molecular weight of the PLGA polymer is more than 100 kDa, more than 200 kDa, more than 300 kDa, more than 400 kDa, or more than 500 kDa.

In embodiments where the bioabsorbable tissue support comprises a PLGA bioabsorbable polymer matrix, incorporation of antibacterial materials, antifungal materials, antimicrobial materials, or other medical chemicals into the PLGA polymer matrix requires a low temperature to incorporate the chemicals into the polymer matrix. In some embodiments, the PLGA polymer matrix requires a temperature of between 5° C. and 15° C. for incorporating the antibacterial materials, antifungal materials, antimicrobial materials, or other medical chemicals.

In one embodiment, the bioabsorbable tissue support (110, 120, 130) can consist of the at least one bioabsorbable material and include a non-bioabsorbable material. In one embodiment, the matrix material may not be employed, and the bioabsorbable tissue support (110, 120, 130) can consist of at least one functional bioabsorbable material. In one embodiment, the at least one bioabsorbable material and/or the matrix can be in a dehydrated state, and addition of water from the tissue may trigger bioabsorption.

Figure 1D:
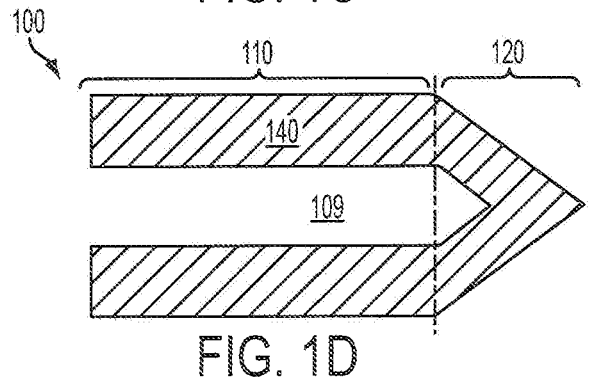
FIG. 1D is a vertical cross-sectional view of a first variation of the first exemplary device including a bioabsorbable tissue support.

Referring to FIG. 1D, a first variation of the first exemplary device 100 is shown, which includes a bioabsorbable tissue support (110, 120) consisting of an elongated portion 110 and the pointed tip portion 120, and does not include an end plate.

Referring to FIG. 1D, a first variation of the first exemplary device 100 is shown, which includes a bioabsorbable tissue support (110, 120) consisting of an elongated portion 110 and the pointed tip portion 120, and does not include an end plate.

Figure 1E:
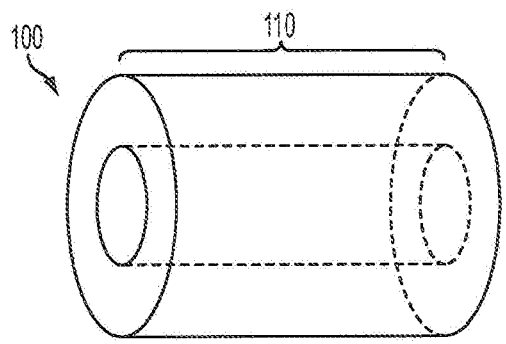
FIG. 1E is an angled view of a second variation of the first exemplary device including a bioabsorbable tissue support.

Referring to FIG. 1E, a second variation of the first exemplary device 100 is shown, which includes a bioabsorbable tissue support 110 consisting of an elongated portion 110, and not including a pointed tip portion or an end plate.

Figure 1F:
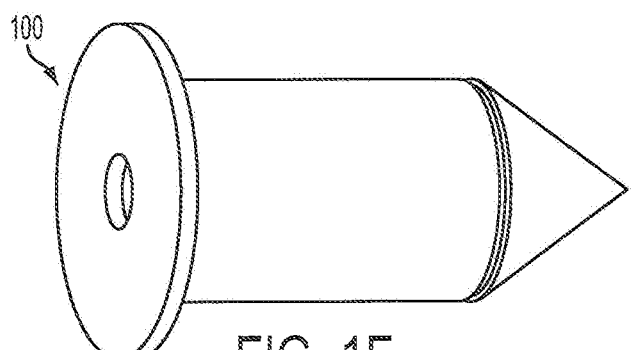
FIG. 1F is an angled view of a third variation of the first exemplary device including a bioabsorbable tissue support.

Referring to FIG. 1F, a third variation of the first exemplary device 100 is shown, which includes a bioabsorbable tissue support (110, 120, 130) that includes a circumferential notch provided between the elongated portion 110 and the pointed tip portion 120. The entirety of the bioabsorbable tissue support (110, 120, 130) is of integral construction, i.e., in a single contiguous piece. The thickness of the region between the elongated portion 110 and the pointed tip portion 120 is reduced relative to the thickness of the elongated portion 110 to provide the circumferential notch. The circumferential notch functions as a self-aligned cutting region after the pointed tip portion 120 of the bioabsorbable tissue support (110, 120, 130) passes through a puncture in a tissue to facilitate detachment of the pointed tip portion 120 from the elongated portion 110. While a circumferential notch is illustrated herein, embodiments are expressly contemplated herein which employ at least one notch that does not encompass a complete circumference and is provided between the elongated portion 110 and the pointed tip portion 120.

Figure 1G:
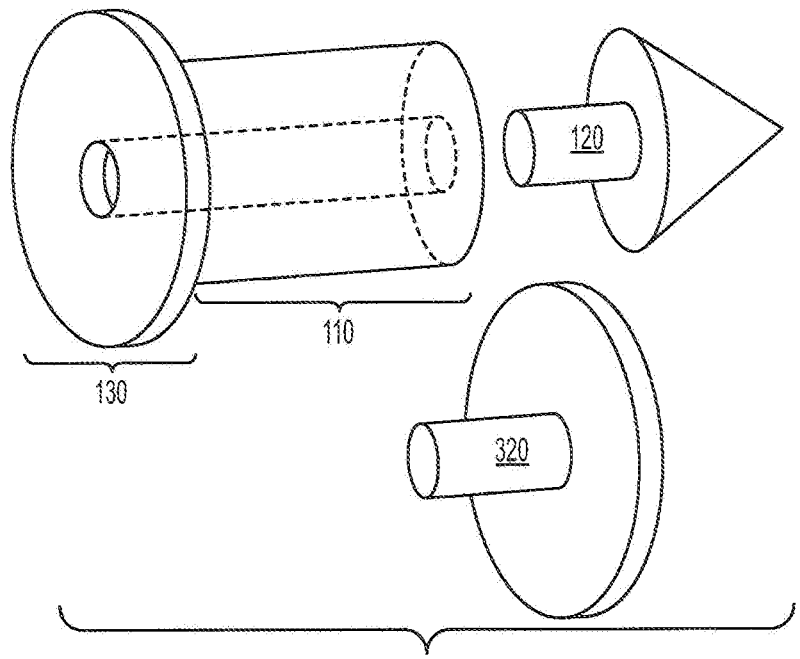
FIG. 1G is an angled view of a fourth variation of the first exemplary device including a bioabsorbable tissue support that includes a detachable pointed tip and a plug plate that can replace the detachable pointed tip upon installation of the bioabsorbable tissue support on a tissue.

Referring to FIG. 1G, a fourth variation of the first exemplary device 100 is shown, which includes a bioabsorbable tissue support (110, 120, 130) that includes a pointed tip portion 120 that is configured to be detachable. For example, the pointed tip portion 120 can have a columnar protrusion that fits into a cavity within the elongated portion 110 at the time of insertion into a through hole in a tissue, removed after insertion into the through hole, and is replaced with a plug plate 320, which can be a flange, a rivet, or an adornment fixture. If the pointed tip portion 120 is not present in the first exemplary device 100, the plug plate 320 can be inserted into the cavity 109 within the elongated portion 110. The plug plate 320 may be composed of a bioabsorbable material, a non-bioabsorbable material, or a combination of a bioabsorbable material configured to contact a tissue and a non-bioabsorbable material configured to provide mechanical support to the bioabsorbable material.

The first exemplary device 100, or any of the devices to be subsequently described in the present disclosure, can be inserted into a through-hole in a tissue portion of a lifeform. The insertion of a device of the present disclosure can be performed simultaneously with formation of a through hole, or after formation of a through hole.

If the insertion of the device of the present disclosure is performed simultaneously with the formation of the through-hole, the device of the present disclosure can be loaded with a pin for forming a puncture through the tissue, and can be loaded into a machine for puncturing the tissue. The device of the present disclosure may be loaded as a core of a bullet that includes a thin rigid shell (not shown) that is employed to form the puncture and subsequently removed, or may be loaded as a back portion of a compound bullet that includes a front portion containing a rigid puncture-forming structure (such as a pin).

If the insertion of the device of the present disclosure is performed after formation of the through-hole, the through-hole may be formed employing any method known in the art, and the device of the present disclosure may be inserted through the through-hole by aligning the device with respect to the through-hole, and by pushing the device into the through-hole. If an end plate 130 (See FIGS. 1A-1C) is present, the end plate 130 can function as a stopping structure to prevent passing of the device through the through-hole.

For any of the first exemplary device 100 or the variations thereof or any of the subsequent devices of the present disclosure to be described below, the entirety of the bioabsorbable tissue support (110, 120, 130) can be of unitary construction, i.e., in a single contiguous structure, or may be manufactured as two or more discrete components, and may be assembled, for example, by screwing, plugging, bonding, and/or molding by partial melting and reflow. For example, the pointed tip portion 120 may be manufactured as a discrete component, and the combination of the elongated portion 110 and the end flange 130 may be manufactured as another discrete component for subsequent assembly with the pointed tip portion 120. Likewise, the end flange 130 may be manufactured integrally with the elongated portion 110, or can be manufactured as a discrete component and affixed to the elongated portion 110.

The first exemplary device 100 or any device of the present disclosure may be stored in a sterile environment before the time of use, and can be loaded into a machine configured to insert the device into a through-hole in a tissue, or can be manually picked up for insertion into the through-hole in the tissue.

Figure 2A:
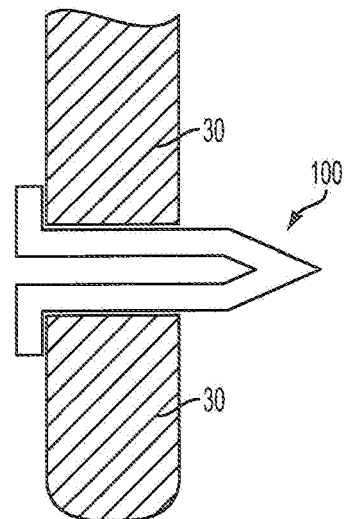
FIG. 2A is an illustration of a configuration in which a device including a bioabsorbable tissue support is inserted through a hole through a tissue of a subject.

Referring to FIG. 2A, a configuration is illustrated in which a first exemplary device 100 including a bioabsorbable tissue support (110, 120, 130; See FIGS. 1A-1C), or any of the devices to be subsequently described in the present disclosure, is inserted through a hole that has been formed through the tissue 30 of a subject. If the bioabsorbable tissue support (110, 120, 130) includes a pointed tip portion 120 and the end plate 130, the boundary between the elongated portion 110 and the end plate 130 can be located on one side of the tissue 30 at, or away from, a first plane including a surface of the tissue 30, and the boundary between the elongated portion 110 and the pointed tip portion 130 can be on the opposite side of the tissue at, or away from, a second plane including another surface of the tissue 30.

Figure 2B:
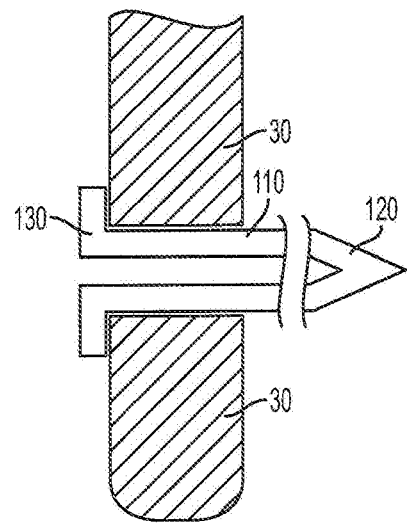
FIG. 2B is an illustration of a configuration in which an integrated pointed top portion of the bioabsorbable tissue support has been cut off.

Referring to FIG. 2B, the pointed tip portion 120, if present within the device of the present disclosure, can be disengaged from the tissue support by unscrewing it or unsnapping it or by employing a cutting apparatus such as a pair of scissors or a knife after insertion of the device through the through-hole. Detachment of the pointed tip portion 120, if present, from the elongated portion causes the cavity 109 to be contiguously connected to the ambient at both sides of the through-hole. Optionally, the end plate 130, if present, may be removed before, or after, detachment of the pointed tip portion 120.

Figure 2C:
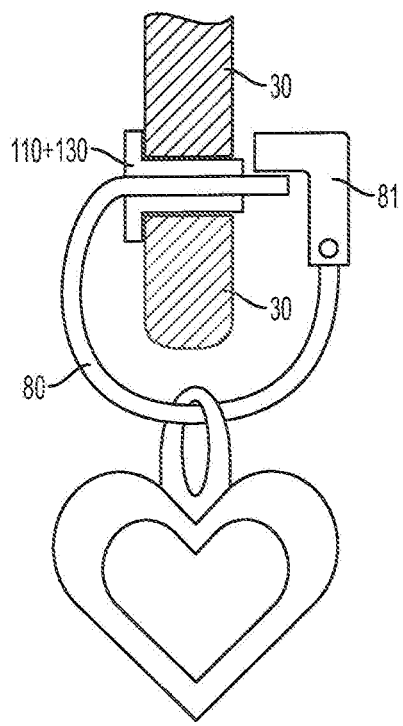
FIG. 2C is an illustration of a configuration in which an earring has been affixed to an ear of a subject employing a device including a bioabsorbable tissue support of the present disclosure.

Referring to FIG. 2C, once the cavity within the device connects to the ambient on both sides of the through-hole, an attachment 80 can be physically attached to the tissue 30 employing an attachment mechanism 81 provided within the attachment 80, or can be added to the attachment 80. For example, an earring may be provided with a pin and a locking mechanism such that the pin can pass through the cavity within the device of the present disclosure and subsequently secured by the locking mechanism. In another example, a flexible thread may be added to an identification tag such that the thread passes through a hole through the identification tag. The thread can further pass through the through-hole within the device of the present disclosure to secure the identification tag to the tissue 30.

In one embodiment, the bioabsorbable tissue support of the present disclosure can include a bioabsorbable dye, and at least one material selected from the group including therapeutic medical chemicals, anesthetic materials, and antiproliferative agents. The bioabsorption of the bioabsorbable tissue support of the present disclosure can be monitored by observing the color of the region including the through-hole. Specifically, the completion of bioabsorption of the materials of the bioabsorbable tissue support can be detected when the color of the region including the through-hole does not include the color of the bioabsorbable dye.

A cavity 109 extends through the elongated portion 110. In one embodiment, the elongated portion 110 can be a tubular structure with two openings, which include one opening at an interface with a pointed tip portion 120, and another opening at an interface with an end plate 130. In one embodiment, the elongated portion 110 can be of integral construction and consist of a single contiguous material portion.

Figure 2D:
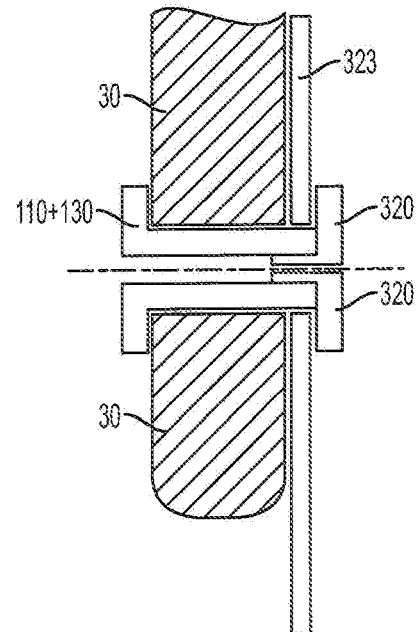
FIG. 2D is an illustration of a configuration in which a plug plate is employed to secure an identification tag upon installation of a device of the present disclosure on a tissue of a subject.

Referring to FIG. 2D, an alternate configuration after installation of the first exemplary device 100 or a variation thereof is illustrated, in which a bioabsorbable tissue support (110, 120, 130) including a detachable pointed tip portion 120 (See FIG. 1G) is employed. In one embodiment, the detachable pointed tip portion 120 may be a discrete component that is plugged into the elongated portion 110 and remain there by fiction, or may be of integration construction with the elongated portion 110 at a structurally weak junction such as a perforation region. The detachable pointed tip potion 120 may be plugged into the elongated portion 110 at the time of insertion through a through hole in a tissue of a subject, and may be detached by pulling out from the elongated portion 110. After removal of the detachable pointed tip portion 120, a tag sheet 323 (which can be an identification tag for an animal) may be hung over a protruding portion of the elongated element 110, and a plug plate 320 can be attached to the remaining portion of the bioabsorbable tissue support (110, 120). The plug plate 320 can be a flange, a rivet, or an adornment fixture. The plug plate 120 may be held in place by friction once installed into the elongated portion 110. The plug plate 320 may have a protruding portion that fits into the cavity in the elongated portion 110, for example, by a clamping device. The plug plate 320 may be composed of a bioabsorbable material, a non-bioabsorbable material, or a combination of a bioabsorbable material configured to contact a tissue and a non-bioabsorbable material configured to provide mechanical support to the bioabsorbable material. A hole may, or may not, be present through the plug plate 320.

According to an embodiment of the present disclosure, a plug plate 320 may be provided in conjunction with any of the devices of the present disclosure that are described above or below. If a pointed tip portion 120 (or an equivalent structure) is provided in any device of the present disclosure, a plug plate 320 may be provided as a discrete component that is not physically contiguous with the device of the present disclosure. If a pointed tip portion 120 (or an equivalent structure) is not attached to an elongated portion 110, a plug plate 320 may be provided as a discrete component not physically attached to the elongated portion 110, or may be provided as plugged into an end region of the elongated portion 110.

In general, the present invention provides a set of structural components for a device that includes a bioabsorbable tissue support and a plug plate 320. The bioabsorbable tissue support contains at least one bioabsorbable material, includes an elongated portion having a uniform or tapered cross-sectional shape, is configured to contact an inner surface of a puncture in a tissue, and has a rigidity to maintain an original shape until the at least one bioabsorbable material is absorbed into a body of a subject to which the device is inserted. Each of the at least one bioabsorbable material may be selected from a group consisting of therapeutic medical chemicals, anesthetic materials, dye materials, and antiproliferative agents. The plug plate 320 is configured to fit into an opening at one end of the elongated portion and includes a portion that, upon union with the elongated portion at an end region thereof, raidally extends farther outward than outer surfaces of the elongated portion from an axis passing through a geometrical center of the elongated portion along the lengthwise direction of the elongated portion. As used herein, the geometrical center of an object is defined by a set of coordinates (xc, yc, zc) in a Cartesian coordinate system such that:

$$x_c = \frac{\int_V x dV}{\int_V dV}; y_c = \frac{\int_V y dV}{\int_V dV}; z_c = \frac{\int_V z dV}{\int_V dV},$$

wherein the integration is performed over the entire volume V of the device. The plug plate 320 may have a configuration of a flange, i.e., a plate having a uniform thickness and confined between a pair of parallel planes.

The plug plate 320 may optionally include an opening therethrough. The plug plate 320 may be plugged into an end region of the elongated portion, or may be provided as a discrete component that is physically detached from the device In one embodiment, the elongated portion 110 can include a plurality of disjoined portions that are connected through a pointed tip portion 120 and/or an end plate 130.

Referring to FIG. 2E, yet another configuration after installation of the first exemplary device 100 or a variation thereof is illustrated. In this configuration, the end flange 130 may be attached to the elongated portion 110 by threading, plugging, latching, or any other mechanical means of attaching one mechanical element to another mechanical element. A pointed tip portion 120 may, or may not, be provided prior to installation of the first exemplary device 100 (or a variation thereof), and subsequently removed, if present after installation. A plug plate 320 may be attached to another end of the elongated portion 110 after insertion of the first exemplary device 100 through a through hole in a tissue 30 by threading, plugging, latching, or any other mechanical means of attaching one mechanical element to another mechanical element. In one embodiment, the end flange 130 and the plug plate 320 may have similar or identical configurations such as a configuration of a holed flange with a protruding thread through which the hole extends.

Referring to FIG. 2F, still another configuration during installation of the first exemplary device 100 or a variation thereof is illustrated. At least one side of the first exemplary device 100 as installed has an end region of the elongated portion 110. For example, both a pointed tip portion 120 and an end plate 130 may be absent after installation (by removal after installation or by being absent prior to installation), or an end plate 130 may be present and a pointed tip portion 120 may not be present. Referring to FIG. 2G, a crimping device 70 including a conical tip on each side or on the side applied to an end region of the elongated portion 110 can be employed to flatten one or both end regions of the elongated portion 110 so that one or two flattened flanges having radially decreasing thickness may be formed.

Figure 3A:
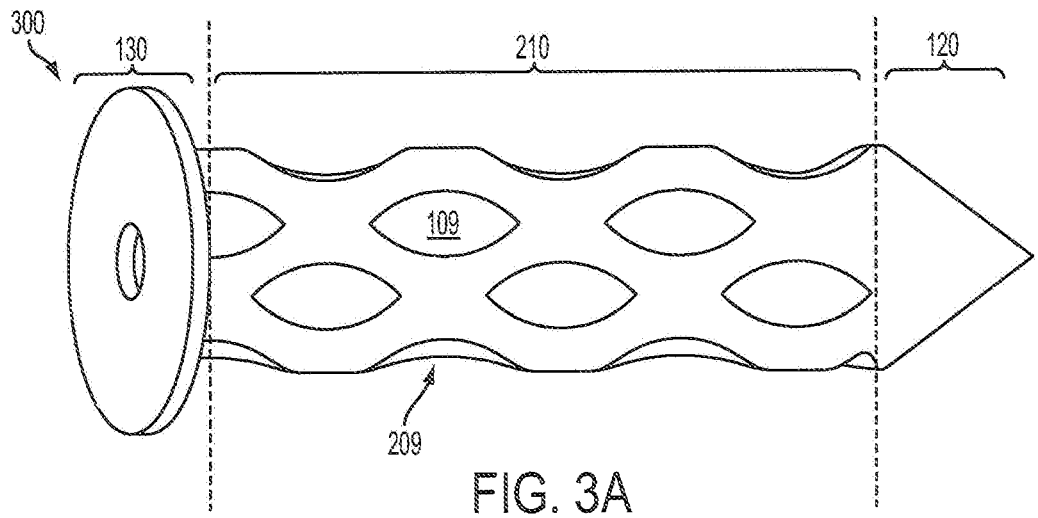
FIG. 3A is an angled view of a second exemplary device including a bioabsorbable tissue support that contains a plurality of openings within an elongated portion.
Figure 3B:
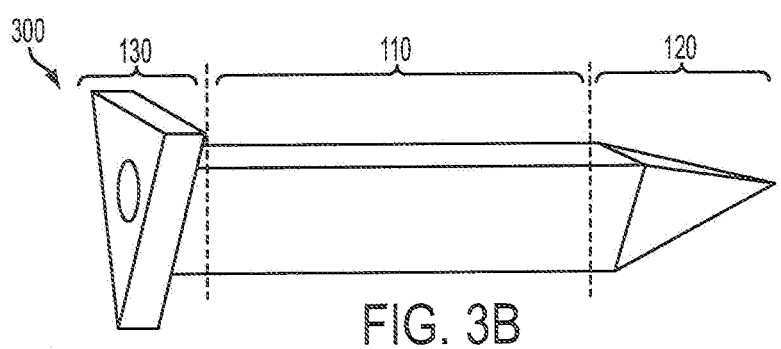
FIG. 3B is an angled view of a type of a third exemplary device including a bioabsorbable tissue support.
Figure 3C:
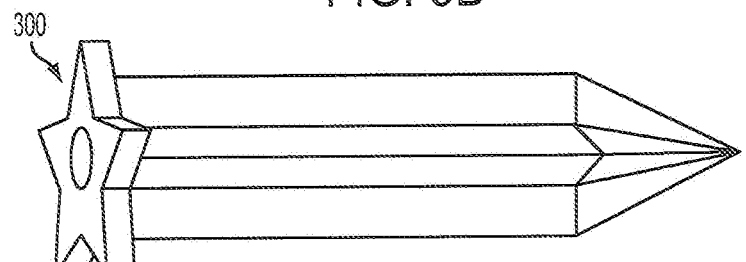
FIG. 3C is an angled view of another type of the third exemplary device including a bioabsorbable tissue support.
Figure 3D:
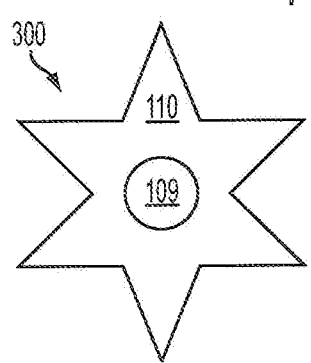
FIG. 3D is a vertical cross-sectional view of yet another type of the third exemplary device including a bioabsorbable tissue support along a vertical plane that passes through an elongated portion in a direction that is perpendicular to the lengthwise axis of an elongated portion.
Figure 3E:
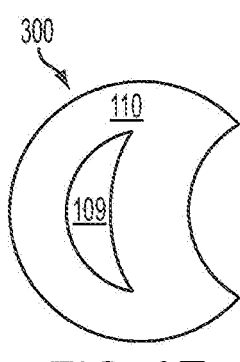
FIG. 3E is a vertical cross-sectional view of still another type of the third exemplary device including a bioabsorbable tissue support along a vertical plane that passes through an elongated portion in a direction that is perpendicular to the lengthwise axis of an elongated portion.
Figure 3F:
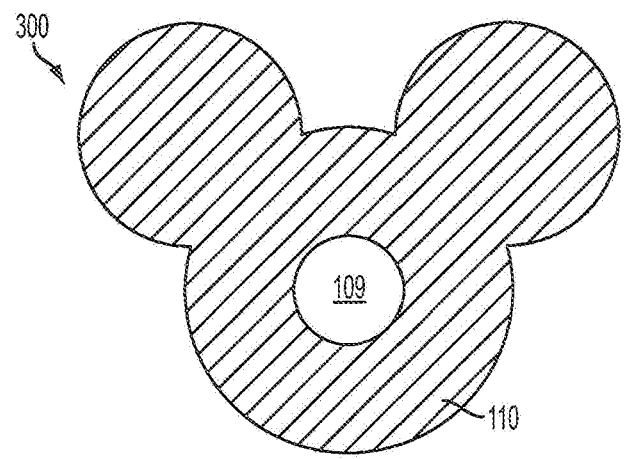
FIG. 3F is a vertical cross-sectional view of even another type of the third exemplary device including a bioabsorbable tissue support along a vertical plane that passes through an elongated portion in a direction that is perpendicular to the lengthwise axis of an elongated portion.

Referring to FIG. 3A, a second exemplary device 200 of the present disclosure includes a bioabsorbable tissue support (210, 120, 130) that contains a plurality of openings 209 within an elongated portion 210. The center portion of the elongated portion is hollow to provide a cavity 109 therein. Each of the plurality of openings 209 through the surfaces of the elongated portion 210 can be connected to the cavity 109 within the elongated portion 210. Thus, the elongated portion 210 has a tubular mesh structure with a plurality of openings 209 through the walls of a generally tubular structure. Each "strand" of the tubular mesh structure can have a sufficient cross-sectional area to prevent collapse of the tubular mesh structure during insertion of the second exemplary device 200 into a through-hole of a tissue (See FIG. 2A) or during the bioabsorption of the bioabsorbable tissue support (210, 120, 130).

If the elongated portion 110 of the first exemplary device includes a uniform or tapered cross-sectional shape, the uniform or tapered cross-sectional shape may have a circular inner periphery or a non-circular inner periphery. Further, the uniform or tapered cross-sectional shape may have a circular or a non-circular outer periphery.

The cross-sectional shape of the tubular structure along the direction perpendicular to the lengthwise axis can be annular, can include at least one elliptical shape and/or a superelliptical shape, can include a polygonal shape, or can including combinations of various curvilinear shapes.

Referring to FIGS. 3B-3F, various types of a third exemplary device 300 including a bioabsorbable tissue support (110, 120, 130) is shown. The elongated portion 110 of the bioabsorbable tissue support (110, 120, 130) can have various vertical cross-sectional shapes that may be uniform or tapered, i.e., invariant, magnified, or reduced with translation along the lengthwise direction of the elongated portion 120. Further, the pointed tip portion 120, if present, of the bioabsorbable tissue support (110, 120, 130) can have a tapered profile of various shapes. In addition, the end plate 130, if present, of the bioabsorbable tissue support (110, 120, 130) can have various shape, which can be polygonal, elliptical, or non-polygonal and non-elliptical. The outer periphery of the end plate 130 may, or may not, be a magnified shape derived from the shape of the outer periphery of the elongated portion 120.

The outer periphery of the vertical cross-sectional shape of the elongated portion 110 can be polygonal, curvilinear, or a shape including a polygonal portion and a curvilinear portion. The outer periphery of the vertical cross-sectional shape of the elongated portion 110 can have a decorative, artistic, and/or fanciful shape. Further, the outer periphery of the end plate 130, if present, can have a decorative, artistic, and/or fanciful shape.

Figure 4A:
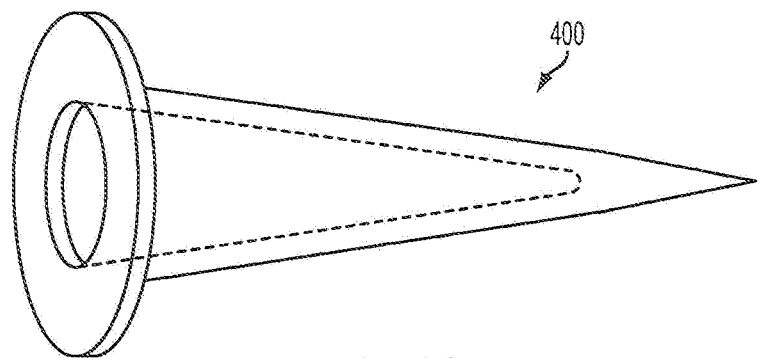
FIG. 4A is an angled view of a first type of a fourth exemplary device including a bioabsorbable tissue support.
Figure 4B:
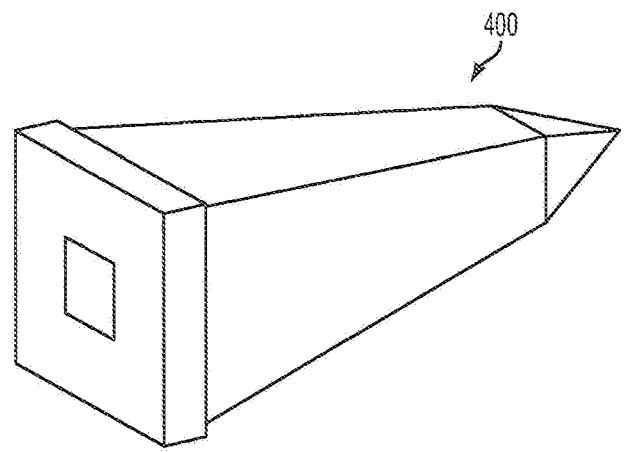
FIG. 4B is an angled view of a second type of the fourth exemplary device including a bioabsorbable tissue support.

Referring to FIGS. 4A and 4B, types of a fourth exemplary device 400 are illustrated. A fourth exemplary device 400 can include a tapered elongated portion in which the shape of the outer periphery of the vertical cross-sectional shape along a direction perpendicular to the lengthwise direction of the elongated portion changes along the lengthwise direction. In one embodiment, the tapered elongated portion can have a uniform taper, i.e., a uniform slope of the outer periphery in an axial cross-sectional view along a plane including the lengthwise axis. In another embodiment, the tapered elongated portion can have a non-uniform taper. In one embodiment, the outer periphery of the vertical cross-sectional shape of the tapered elongated portion can shrink with translation toward the pointed tip portion.

Figure 5:
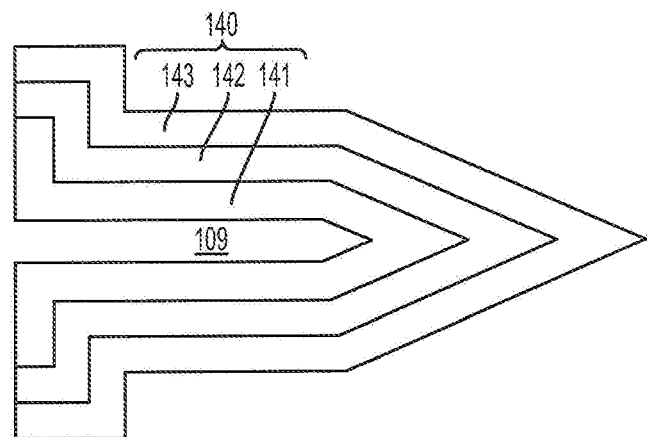
FIG. 5 is a vertical cross-sectional view of a bioabsorbable tissue support that illustrates a layered structure including multiple layers of bioabsorbable materials.

Referring to FIG. 5, a vertical cross-sectional view of a bioabsorbable tissue support 140 is shown. The bioabsorbable tissue support 140 can have any configuration for the bioabsorbable tissue support previously described. The bioabsorbable tissue support 140 can be any of the devices of present disclosure that is previous or subsequently described herein. The bioabsorbable tissue support 140 can have a homogeneous composition including at least one bioabsorbable material, or can have a layered structure including multiple layers of bioabsorbable materials.

In one embodiment, the at least one bioabsorbable material can includes a plurality of layers (141, 142, 143) having different compositions. In one embodiment, the plurality of layers (141, 142, 143) can include at least a first layer 141 having a first composition having a first bioabsorption half-life, and a second layer 142 surrounded by the first layer 141 and having a second composition having a second bioabsorption half-life that is longer than the first bioabsorption half-life. The first layer 141 can be an outer layer for the second layer 142, which can be an inner layer. The first bioabsorption half-life can be in a range from 1 hour to 1 week, and the second bioabsorbable half-life can be in a range from 1 day to 10 weeks, although lesser and greater time periods for the first bioabsorption half-life and the second bioabsorption half-life can also be employed.

In one embodiment, the plurality of layers (141, 142, 143) can include a first layer 141 providing a first functionality, and a second layer 142 providing a second functionality that is different from the first functionality. For example, the first layer 141 can provide a first functionality selected from a group including, or consisting of, therapeutic treatment of the puncture, anesthetic treatment of the puncture, coloring of a region around the puncture, and prevention of change of shape of the puncture; and the second layer 142 can provide a second functionality selected from including, or consisting of, therapeutic treatment of the puncture, anesthetic treatment of the puncture, coloring of a region around the puncture, and prevention of change of shape of the puncture, such that the second functionality is different from the first functionality. At least one additional layer 143 can be present on the inside or outside of the stack of the first layer 141 and the second layer 142.

The thickness of each layer (141, 142, or 143) as measured in an elongated region can be in a range from 1 micron to 2 mm, although lesser and greater thicknesses can also be employed. The total thickness of the plurality of layers (141, 142, 143) as measured in an elongated region can be in a range from 0.5 mm to 3 mm, although lesser and greater thicknesses can also be employed.

The various bioabsorbable tissue supports of the present disclosure can be manufactured by various methods including, but not limited to, extrusion, stamping, molding, three-dimensional printing, laser cutting, laser welding, deposition of a material in vacuum or in a gas ambient, coating, and combinations thereof.

Figure 6A:
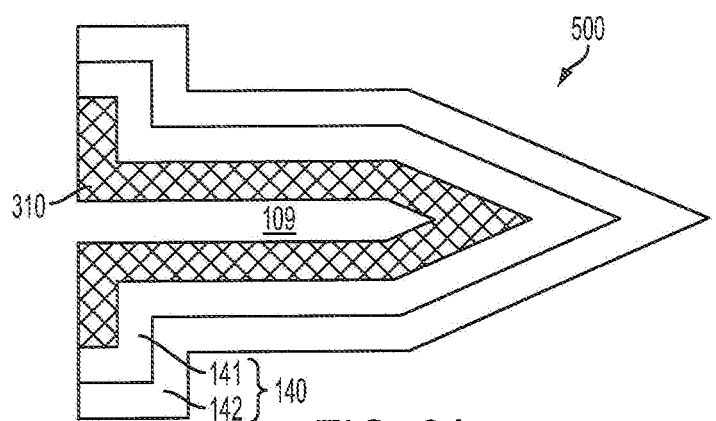
FIG. 6A is a vertical cross-sectional view of a fifth exemplary device including a bioabsorbable tissue support and a non-bioabsorbable tissue support along a vertical plane containing a lengthwise axis of an elongated portion.

Referring to FIG. 6A, a fifth exemplary device 500 includes a bioabsorbable tissue support 140 and a non-bioabsorbable tissue support 310. The non-bioabsorbable tissue support 310 includes at least one non-bioabsorbable material, and can consist of the at least one non-bioabsorbable material. The non-bioabsorbable tissue support 310 can have a configuration of a liner located on the entire inner surfaces of the bioabsorbable tissue support 140. The cavity 109 is spaced from the bioabsorbable tissue support 140 by the non-bioabsorbable tissue support 310. In one embodiment, a portion of the non-bioabsorbable tissue support can be located outside of, protrude outward from, the bioabsorbable tissue support 140 (e.g., on the side of an end plate), and can include one or more rivets or a structure attached like a rivet.

The non-bioabsorbable tissue support 310 can be embedded within the bioabsorbable tissue support 140. At least a portion of the bioabsorbable tissue support 140 is located outside of the non-bioabsorbable tissue support 310. In one embodiment, the entirety of the bioabsorbable tissue support 140 can be located outside of the non-bioabsorbable tissue support 310. In one embodiment, the non-bioabsorbable tissue support 310 includes a rigid material that maintains an original shape after the bioabsorbable tissue support 140 is absorbed by the tissue after insertion of the device of the present disclosure into a through-hole.

In one embodiment, the non-bioabsorbable tissue support 310 can have Young's modulus greater than 1 GPa. In one embodiment, the bioabsorbable tissue support 140 can have Young's modulus in a range from 0.01 GPa to 10 GPa. In one embodiment, the bioabsorbable tissue support 140 can have a smaller Young's modulus than the non-bioabsorbable tissue support 310.

In another embodiment, the bioabsorbable tissue support 140 and the non-bioabsorbable tissue support 310 can be a plastic material that is deformable and maintains a deformed shape after removal of a force that causes the deformation.

The non-bioabsorbable tissue support 310 includes an elongated portion that is embedded, and laterally surrounded by, an elongated portion of the bioabsorbable tissue support 140. The geometry of the elongated portion of the non-bioabsorbable tissue support 310 can be any of the geometries for the elongated portion of the bioabsorbable tissue support described above. The non-bioabsorbable tissue support 310 can optionally include a pointed tip portion, which may be embedded, and laterally surrounded by, a pointed tip portion of the bioabsorbable tissue support 140 if the bioabsorbable tissue support includes the pointed tip portion. The geometry of the pointed tip portion of the non-bioabsorbable tissue support 310 can be any of the geometries for the pointed tip portion of the bioabsorbable tissue support described above. The non-bioabsorbable tissue support 310 can optionally include an end plate, which may be embedded, and laterally surrounded by, an end plate of the bioabsorbable tissue support 140 if the bioabsorbable tissue support includes the end plate. The geometry of the end plate of the non-bioabsorbable tissue support 310 can be any of the geometries for the end plate of the bioabsorbable tissue support described above. The dimensions of the non-bioabsorbable tissue support 310 are selected such that the cavity 109 extends through the entirety of an elongated portion of the bioabsorbable tissue support 140.

The fifth exemplary device 500 or the devices of the present disclosure to be subsequently described and include a bioabsorbable tissue support and a non-bioabsorbable tissue support can be formed by separately manufacturing, and subsequently merging, the bioabsorbable tissue support and the non-bioabsorbable tissue support; by forming the bioabsorbable tissue support first and then forming the non-bioabsorbable tissue support on the bioabsorbable tissue support, or by forming the non-bioabsorbable tissue support and then forming the bioabsorbable tissue support on the non-bioabsorbable tissue support.

The thickness of bioabsorbable tissue support 140 as measured in an elongated region can be in a range from 1 micron to 3 mm, although lesser and greater thicknesses can also be employed. The thickness of non-bioabsorbable tissue support 310 as measured in an elongated region can be in a range from 30 microns to 0.5 mm, although lesser and greater thicknesses can also be employed.

Figure 6B:
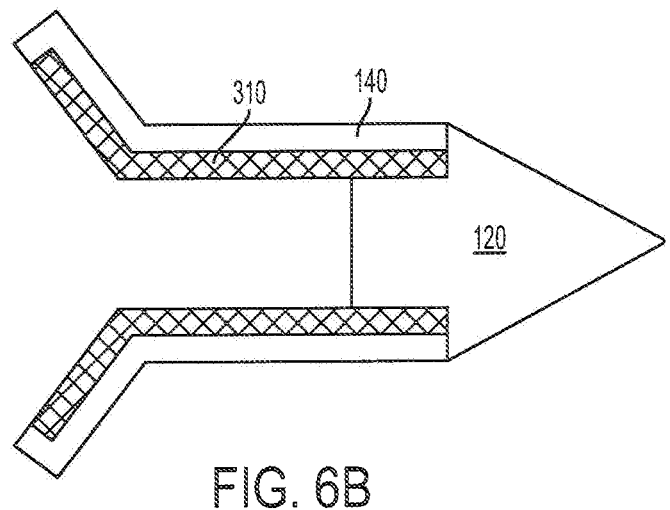
FIG. 6B is a vertical cross-sectional view of a first variation of the fifth exemplary device.

Referring to FIG. 6B, a first variation of the fifth exemplary device is illustrated, which includes an angled end plate made of a malleable material. The pointed tip portion may, or may not, be detachable. In one embodiment, the end plate may have a shape of a frustum, i.e., a cone without the top portion. The end plate may function as a rivet after installation of the device into a through hole in a tissue. Alternatively, the end plate may be fanned, i.e., may be divided into multiple fins along radial directions, i.e., along the directions perpendicular to the axial direction of the elongated portion. The portion of the portion of the non-bioabsorbable tissue support 310 in the end plate can be composed of a malleable material such as a transition metal or aluminum, or an intermetallic alloy of at least two transition metals or an aluminum alloy. The portion of the non-bioabsorbable tissue support 310 in the end plate may, or may not, have the same composition as the rest of the non-bioabsorbable tissue support 310.

Figure 6C:
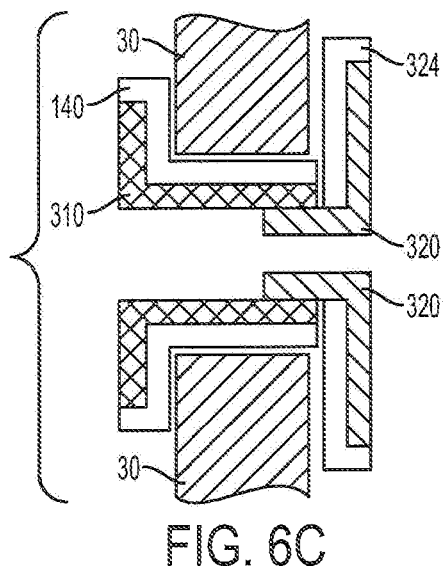
FIG. 6C is a vertical cross-sectional view of the first variation of the fifth exemplary device of FIG. 6B after installation on a tissue.

Referring to FIG. 6C, the first variation of the fifth exemplary device may be installed on a tissue 30 employing methods illustrated in FIGS. 2A, 2B, and 2D. The pointed tip portion is removed. Optionally, a tag may be added if desired. A plug plate 320 is added to a region from which the pointed tip portion has been removed. After installation, the end portion can be deformed, for example, by hammering or by pressing, so that the surfaces of the rivet 330 can press against surfaces of the tissue 30. The plug plate 320 may be composed of a bioabsorbable material, a non-bioabsorbable material, or a combination of a bioabsorbable material configured to contact a tissue and a non-bioabsorbable material configured to provide mechanical support to the bioabsorbable material. Optionally, a bioabsorbable material coating layer 324 may be provided on a surface of the plug plate 320 that is proximal to the tissue 30. A hole may, or may not, be present through the plug plate 320.

Figure 6D:
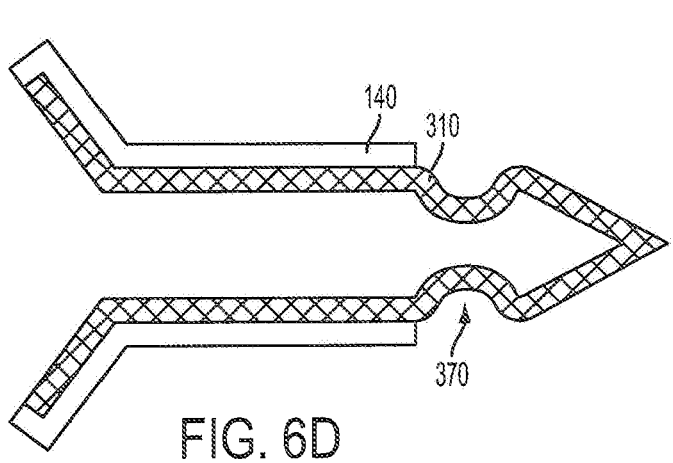
FIG. 6D is a vertical cross-sectional view of a second variation of the fifth exemplary device.

Referring to FIG. 6D, a second variation of the fifth exemplary device is illustrated, which includes an elastic neck 370 between an elongated portion of the non-bioabsorbable tissue support 310 and a pointed tip portion of the non-bioabsorbable tissue support 310.

Figure 6E:
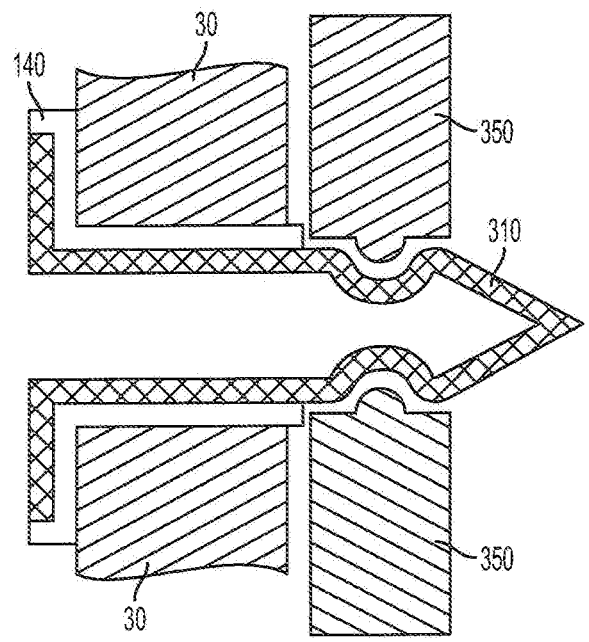
FIG. 6E is a vertical cross-sectional view of the second variation of the fifth exemplary device of FIG. 6D after installation on a tissue.

Referring to FIG. 6E, a crimping device 350 (such as a washer) may be employed at the time of installation of the second variation of the fifth exemplary device such that the neck 370 latched to the washer 350. Optionally, a tag (not shown) may be attached to the crimping device 350, or between the tissue 30 and the crimping device 350 and around the non-bioabsorbable tissue support 310 at the time of installation of the second variation of the fifth exemplary device.

The various non-bioabsorbable tissue supports of the present disclosure can be manufactured by various methods including, but not limited to, extrusion, stamping, molding, three-dimensional printing, laser cutting, laser welding, deposition of a material in vacuum or in a gas ambient, coating, and combinations thereof.

Figure 7A:
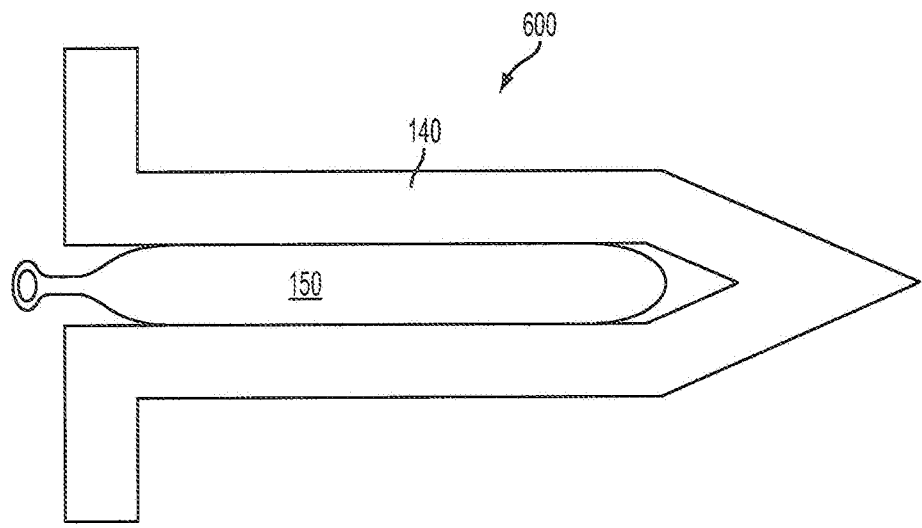
FIG. 7A is a vertical cross-sectional view of a first type of a sixth exemplary device including a bioabsorbable tissue support and a balloon along a vertical plane containing a lengthwise axis of an elongated portion.
Figure 7B:
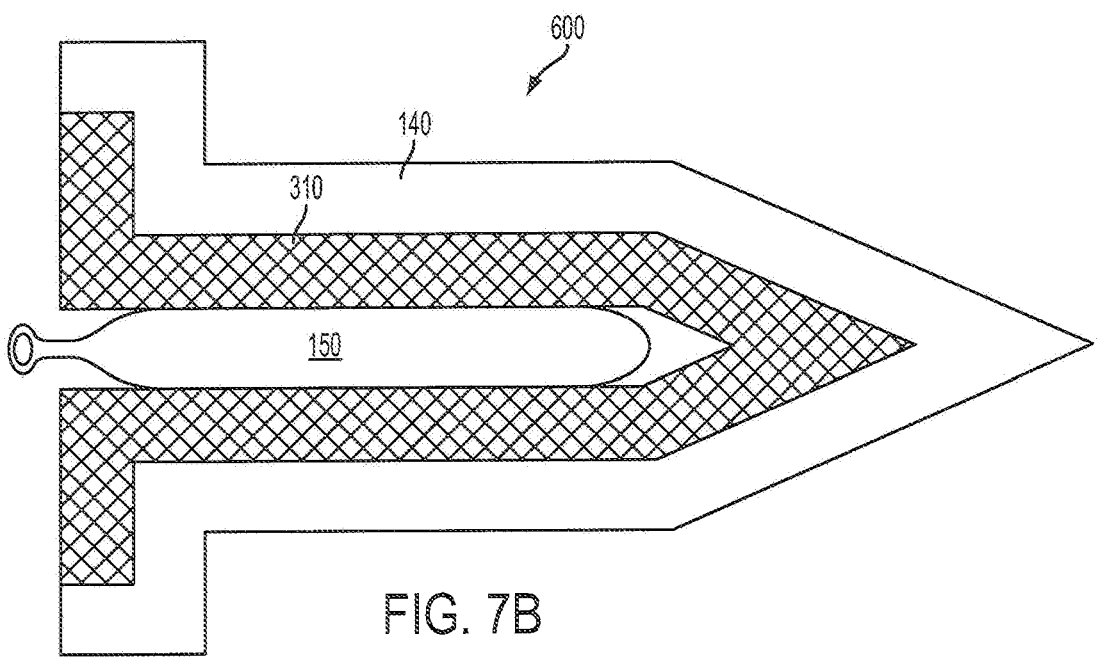
FIG. 7B is a vertical cross-sectional view of a second type of the sixth exemplary device including a bioabsorbable tissue support, a non-bioabsorbable tissue support, and an expansion device along a vertical plane containing a lengthwise axis of an elongated portion.

Referring to FIGS. 7A and 7B, types of a sixth exemplary device 600 are illustrated. The sixth exemplary device 600 includes any of the devices of the present disclosure as described above, and further includes an expansion-inducing device 150. A predominant portion of the expansion-inducing device 150 that does not include a fitting portion 151 is embedded within the cavity 109 inside the elongated portion of the device. The fitting portion 151 can be a structure configured to attach the expansion-inducing device 150 to an external device configured to trigger the expansion of the expansion-inducing device 150. The expansion-inducing device 150 can be any device that can induce expansion of the sixth exemplary devices 600. In one embodiment, the expansion-inducing device can be a balloon that expands upon injection of a fluid. In this case, the fitting portion 151 can be an opening of the balloon, which is a tube fitting portion configured to receive an end portion of a tube. The balloon can be made of any material that can be inflated upon injection of a fluid therein. As used herein, a fluid collectively refers to a gas and a liquid.

As used herein, a "expansion-inducing device" includes a balloon, a coil, a spring, or combinations thereof.

Figure 7C:
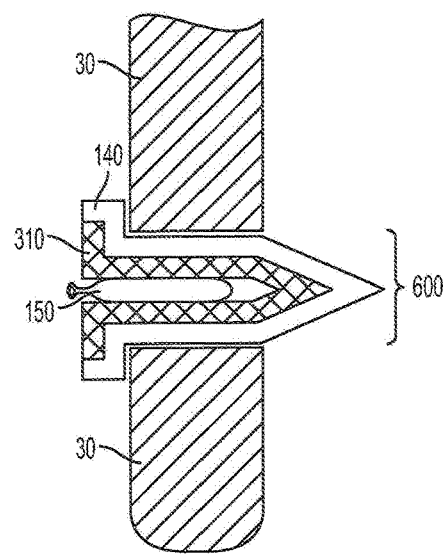
FIG. 7C is a vertical cross-sectional view of the sixth exemplary device after insertion into a hole through a tissue of a subject, prior to expansion.

Referring to FIG. 7C, the sixth exemplary device 600 can be inserted into a through-hole in a tissue 30 of a subject. The pointed tip portion, if present, of the sixth exemplary device 600 can be truncated employing a cutting device. The location of the innermost portion of the expansion-inducing device 150 is selected such that truncation of the pointed tip portion does not collaterally damage the integrity of the expansion-inducing device 150.

Alternatively, a device of the present disclosure that does not include an expansion-inducing device can be inserted into a through-hole through a tissue of a subject, and an expansion-inducing device 150 can be subsequently inserted through the cavity 109 within the device. In general, the expansion-inducing device 150 can be provided within the cavity in the elongated portion before, or after, the insertion of a device of the present disclosure.

Figure 7D:
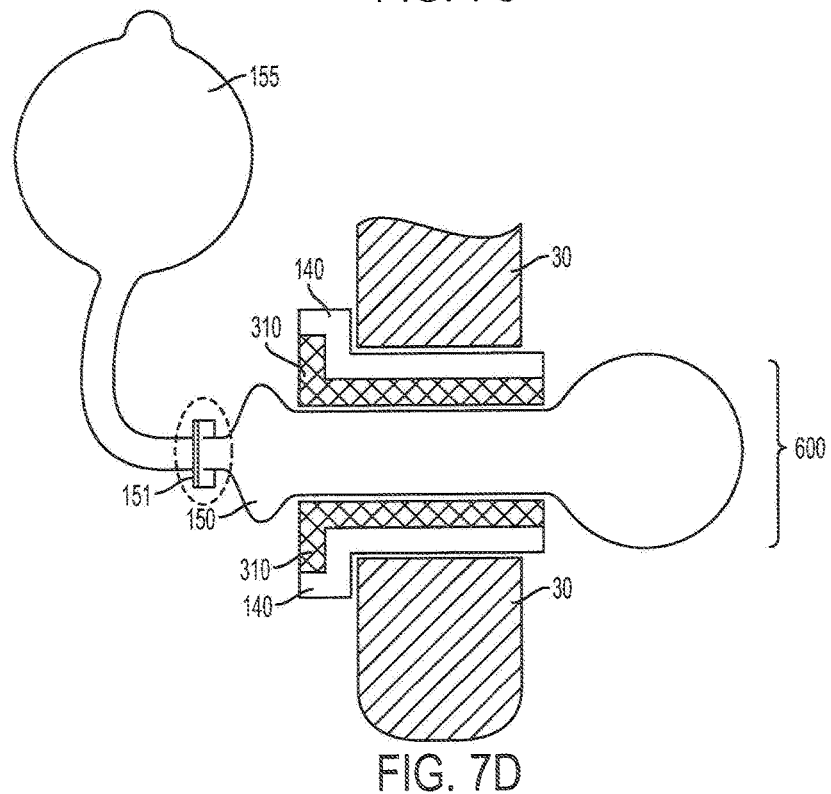
FIG. 7D is a vertical cross-sectional view of the sixth exemplary device after expansion employing an inflation device.

Referring to FIG. 7D, an expansion-activation device 155 can be attached to the fitting portion 151 of the expansion-inducing device 150. In case the expansion-inducing device 150 is a balloon, the expansion-activation device 155 may be an inflation device that supplies a fluid to the inside of a balloon through the fitting portion 151. The inflation device can be a manual air pump, a catheter with a volume control capability, a mechanical air pump with controllable air output, or a liquid pump that can fill the inside of the balloon with a liquid.

The elongated portion of the device of the present disclosure can be outwardly expanded by the expansion-inducing device 150, or similar device for enlarging the tissue support. The non-bioabsorbable tissue support 310 can include a plastic material that is deformed under pressure from the expansion-inducing device 150, and remains deformed after the expansion-inducing device 150 is shrunk or deflated, and then removed. For example, the non-bioabsorbable tissue support 310 can include a metallic material or an organic polymer-based plastic material. The expansion-inducing device 150 and the inflation device 155 can be removed once the size of the outer periphery of the elongated portion of the device reaches a target shape intended by the operator of the expansion-activation device 155.

The expansion-inducing device 150 of the present disclosure can be employed with any device of the present disclosure. It is understood that expansion of the devices of the present disclosure is optional, and the devices of the present disclosure may be employed without expansion. The non-bioabsorbable tissue support in the devices of the present disclosure may stay with the tissue of the subject permanently or temporarily, or may be removed when such a removal is desired.

Figure 7E:
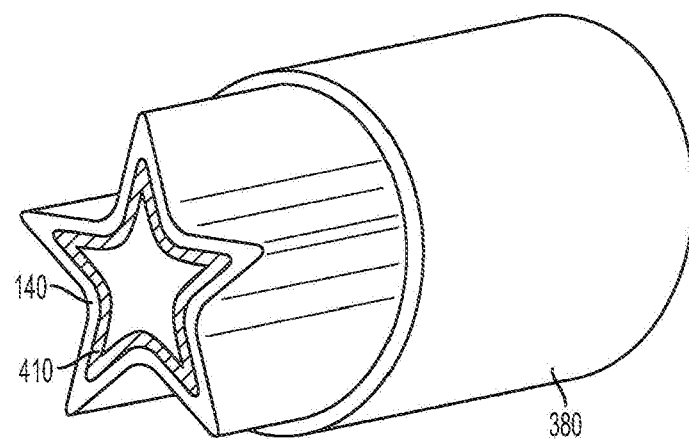
FIG. 7E is a bird's eye view of a first variation of the sixth exemplary device that includes a self-expanding non-bioabsorbable tissue support, a coating of a bioabsorbable tissue support, and a removable sleeve that suppresses expansion of the assembly of tissue supports according to an embodiment of the present disclosure.

Referring to FIG. 7E, a first variation of the sixth exemplary device that includes a spring-loaded non-bioabsorbable tissue support 410, a coating of a bioabsorbable tissue support 140, and a removable sleeve 380 that suppresses expansion of the assembly of tissue supports (410, 140). The spring-loaded non-bioabsorbable tissue support 410 is a self-expanding non-bioabsorbable tissue support that conforms to a shape having a greater cross-sectional area and/or later protrusion from the axial direction upon release of the stored energy within the spring upon removal of the removable sleeve 380 after installation of the first variation of the sixth exemplary device (140, 410, 380) into a through hole in a tissue of a subject. The removable sleeve 380 can include any material such as plastics, ceramics, metallic materials, or combinations thereof, and can have a cylindrical shape. The thickness of the removable sleeve 380 may be selected so that the removable sleeve 380 has sufficient mechanical strength to contain the expansive force applied to the inner sidewalls of the removable sleeve by the spring-loaded non-bioabsorbable tissue support 410.

Figure 7F:
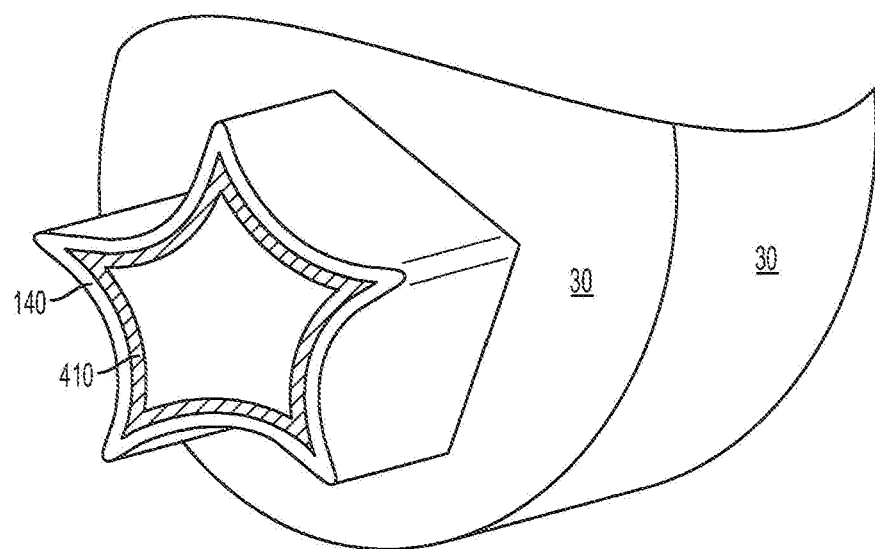
FIG. 7F is a bird's eye view of the first variation of the sixth exemplary device after installation into a through hole in a tissue of a subject and subsequent removal of the sleeve to trigger expansion of the assembly of tissue supports and to induce deformation and/or expansion of the through hole according to an embodiment of the present disclosure.

The spring-loaded non-bioabsorbable tissue support 410 is self-expanding, and the expansive force of the spring-loaded non-bioabsorbable tissue support 410 is counterbalanced by the removable sleeve 380 at the time of installation through the through hole. The removable sleeve 380 can be slid out, thereby causing initiation of expansion of the assembly of tissue supports (410, 140). As illustrated in FIG. 7F, the shape of the through hole may be deformed toward a target shape and/or may be expanded at selected corners. The spring-loaded non-bioabsorbable tissue support 410 is configured to expand upon removal of the removable sleeve 380, and to conform to a target shape upon release of stress in the elastic material. Upon removal of the removable sleeve 380 in a through-hole of a tissue 30, the stress in the spring-loaded non-bioabsorbable tissue support 410 is immediately released so that the through hole gradually changes its shape during the bioabsorption of the at least one bioabsorbable material of the bioabsorbable tissue support 140.

During the shape change of the spring-loaded non-bioabsorbable tissue support 410, the spring-loaded non-bioabsorbable tissue support 410, still containing unrelieved stress, applies pressure at selective regions of sidewalls of the tissue 30 to prevent growth of new tissues therefrom while removing pressure at some other regions of the sidewalls of the tissue 30 to facilitate growth of new tissues therefrom. The growth of new tissues can be thus molded to induce formation of a target shape for the through-hole in the tissue, which can have peripheral surfaces of an arbitrary shape. The through-hole in the tissue 30 may be enlarged at selective regions during the process of the expansion of the spring-loaded non-bioabsorbable tissue support 410, and may shrink at other selective regions during the process of the expansion of the spring-loaded non-bioabsorbable tissue support 410.

Figure 7G:
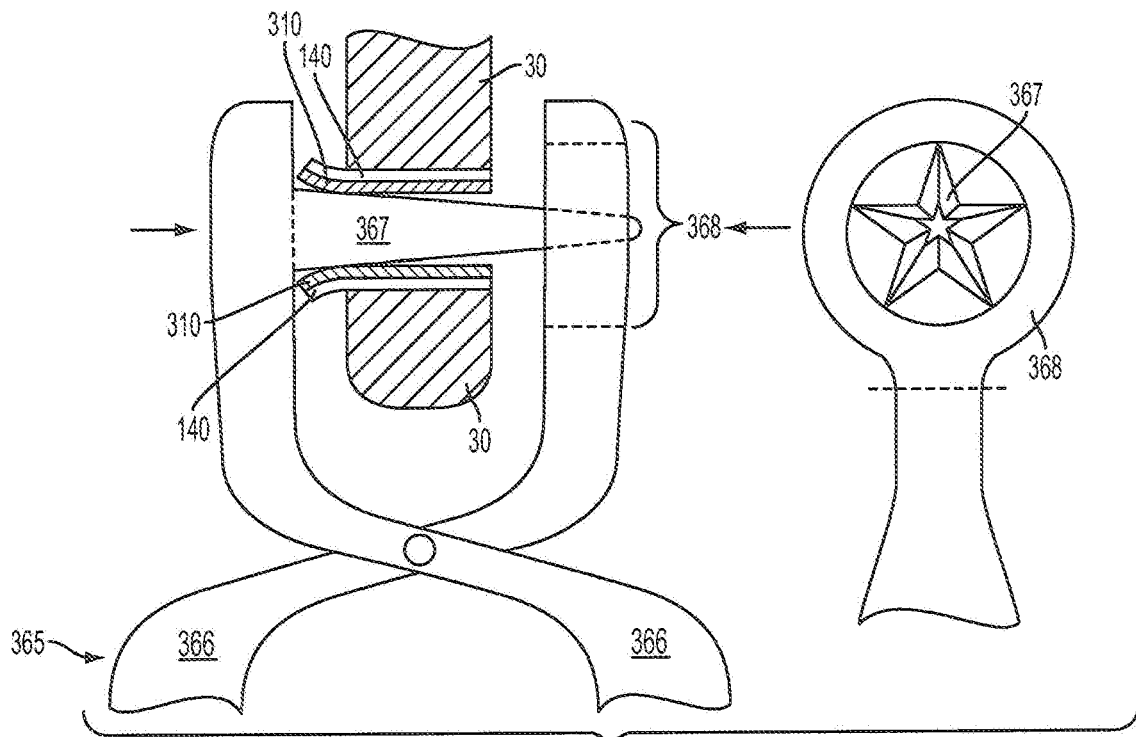
FIG. 7G is schematic view illustrating the process of manual deformation and/or expansion of the assembly of the tissue supports employing a mechanical hole expansion device according to an embodiment of the present disclosure

Referring to FIG. 7G, a size expansion device 365 may be employed to shape and/or enlarge a stand-alone bioabsorbable tissue support 140 or a combination of a bioabsorbable tissue support 140 and a non-bioabsorbable tissue support 310. The size expansion device 365 can include, for example, a pair of handled leverage structures 366 configured to pivot around a pivot axis and to apply leveraged force to a target, a frustum 367 having a target shape along a direction perpendicular to the axis and having monotonically decreasing cross-sectional area with distance from a base that is attached to one of the handled leverage structures 366, and a ring 368 configured to mechanically support one end of a stand-alone bioabsorbable tissue support 140 or a combination (140, 310) of tissue supports. By pressing the frustum 340 against the stand-alone bioabsorbable tissue support 140 or a combination (140, 310) of tissue supports while the ring 368 holds one end of the stand-alone bioabsorbable tissue support 140 or the combination (140, 310) of tissue supports, the stand-alone bioabsorbable tissue support 140 or the combination (140, 310) of tissue supports can be expanded to the target size. The expansion to the target size may be performed at the time of installation of the device of the present disclosure, and/or may be performed once or many times after installation of the device of the present disclosure while monitoring the medical condition of the tissue 30 through which the device is installed.

The non-bioabsorbable tissue support of the devices of the present disclosure can be of solid construction, and can be topologically homeomorphic to a torus or a sphere. As used herein, a first element is topologically homeomorphic to a second element if the first element can be contiguously stretched or shrunk without forming any new hole and without destroying any preexisting hole, if any exists.

Figure 8A:
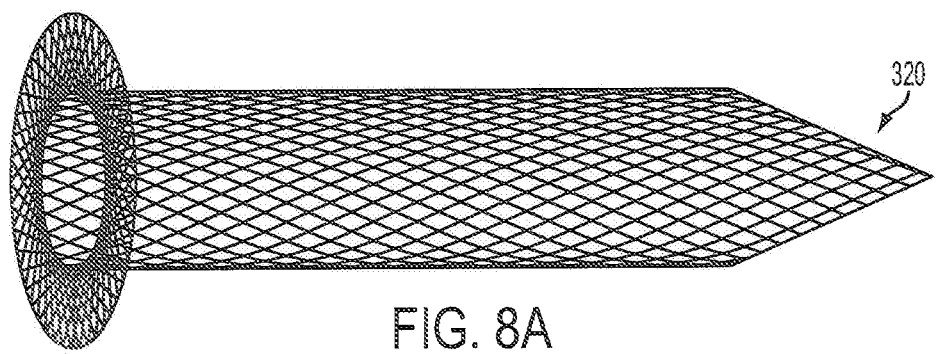
FIG. 8A is an angled view of an exemplary non-bioabsorbable tissue support including pores therein.
Figure 8B:
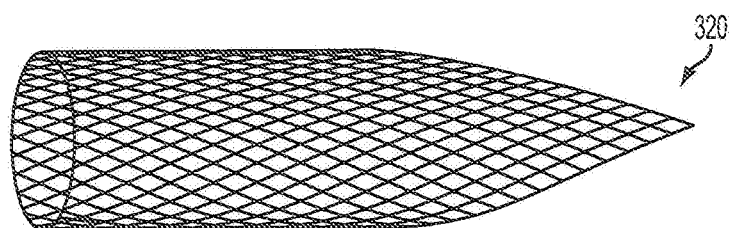
FIG. 8B is an angled view of another exemplary non-bioabsorbable tissue support made of a mesh.

Alternatively, the non-bioabsorbable tissue support of the devices of the present disclosure can include a mesh structure with at least one opening therein. Referring to FIGS. 8A and 8B, exemplary non-bioabsorbable tissue supports made of a mesh 320 are illustrated. The mesh 320 includes pores therein, and can be made of a metallic material, an organic polymer-based plastic material, or a ceramic material. The mesh 320 may employ a mesh or discrete wires that are weaved to form a mesh structure. Alternatively, the mesh 320 of the present disclosure may include a single sheet having holes that generate a general pattern of a mesh, or may include an adjoined structure including multiple sheets having holes that generate a general pattern of a mesh, without employing discrete wires. The non-bioabsorbable tissue support 310 can be of tubular mesh, coil, or similar design characterized by flexibility, compressibility, and expandability. The lateral dimensions of the s or -like portions of a sheet can be in a range from 10 microns to 500 microns, although lesser and greater lateral dimensions can also be employed. In one embodiment, the material and the geometry of the mesh 320 can be selected such that the mesh 320 can expand in a configuration described in FIG. 7D.

Figure 9A:
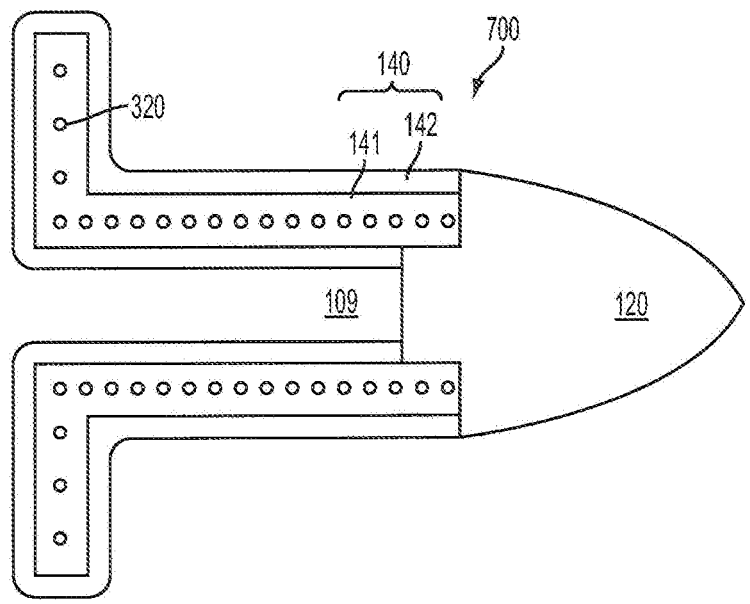
FIG. 9A is a vertical cross-sectional view of a first type of a seventh exemplary device including a non-bioabsorbable tissue support made of a mesh and a bioabsorbable tissue support.
Figure 9B:
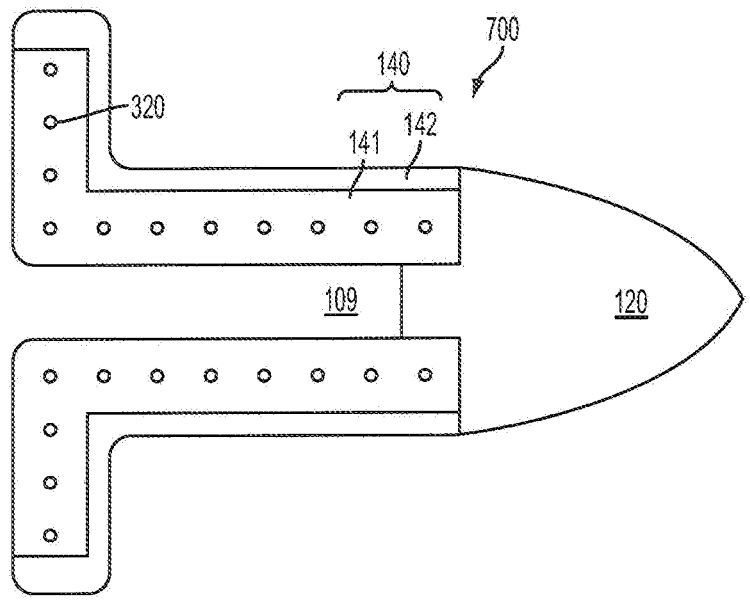
FIG. 9B is a vertical cross-sectional view of a second type of the seventh exemplary device.

Referring to FIGS. 9A and 9B, seventh exemplary devices 700 are illustrated. Each seventh exemplary device 700 includes a non-bioabsorbable tissue support made of a mesh 320 and a bioabsorbable tissue support 140. The mesh 320 can be embedded within the bioabsorbable tissue support 140. If the bioabsorbable tissue support 140 includes a plurality of layers, the mesh 320 can be embedded in one of the layers (e.g., the first layer 141) in the bioabsorbable tissue support 140.

In an illustrative example, the seventh exemplary device 700 can be manufactured by first providing a mesh 320, which can include a rigid material or a plastic material. The bioabsorbable tissue support 140 can be formed as at least one coating layer that is applied to the surfaces of the mesh 320. In one embodiment, an all-surface coating method can be employed in which each successive layer is coated on the entire surfaces of a preceding layer including the inner surfaces physically exposed to the cavity 109 and the outside surfaces as illustrated in FIG. 9A. In another embodiment, an outer-surface-only coating method can be employed in which each successive layer is coated on the outer surfaces of a preceding layer, while not being coated on the inner surfaces facing the cavity 109 as illustrated in FIG. 9B. In yet another embodiment, a combination of an all-surface coating method and an outer-surface-only coating method can be employed.

As discussed above, the different layers in the bioabsorbable tissue support 140 may have different compositions or the same composition. While a configuration in which the elongated portion of the bioabsorbable tissue support 140 is formed as a cylindrical structure without any hole therein, embodiments are expressly contemplated herein in which the elongated portion of the bioabsorbable tissue support 140 is formed as a mesh structure illustrated in FIG. 3A.

Figure 10A:
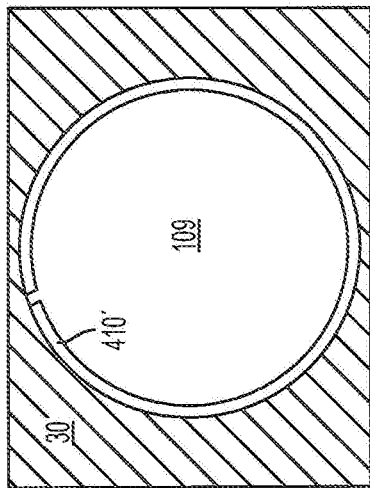
FIG. 10A is a vertical cross-sectional view of an eighth exemplary device employing a spring-loaded non-bioabsorbable tissue support embedded within a bioabsorbable tissue support as inserted within a hole in a tissue.

Referring to FIG. 10A, an eighth exemplary device 800 of the present disclosure includes a spring-loaded non-bioabsorbable tissue support 410 embedded within a bioabsorbable tissue support 140. The spring-loaded non-bioabsorbable tissue support 410 can be an elastic sheet or an elastic mesh that is compressed into a shape surrounding the cavity 109. The spring-loaded non-bioabsorbable tissue support 410 is in a "spring-loaded" shape, which refers to a non-equilibrium shape for an electric structure that returns, upon removal of a constraining force, to a different shape. The bioabsorbable tissue support 140 constrains the spring-loaded non-bioabsorbable tissue support 410 in the spring-loaded shape. In other words, the spring-loaded non-bioabsorbable tissue support 410 is a non-bioabsorbable tissue support including an elastic material that is spring loaded in a compressed state by the bioabsorbable tissue support 140. The spring-loaded non-bioabsorbable tissue support 410 is self-expanding, and the expansive force of the spring-loaded non-bioabsorbable tissue support 410 is counterbalanced by the bioabsorbable tissue support 140 before the bioabsorbable tissue support 140 is absorbed by a tissue 30.

The bioabsorbable tissue support 140 can be formed on the outer surface of the spring-loaded non-bioabsorbable tissue support 410. Alternatively, the spring-loaded non-bioabsorbable tissue support 410 can be inserted into the cavity 109 of a device such as the exemplary devices illustrated in FIGS. 1A-1F, 3A-3F, 4A, and 4B. In one embodiment, the spring-loaded non-bioabsorbable tissue support 410 can be present only within the elongated portion of the devices of the present disclosure, and not present in a pointed tip portion or in an end plate. The eighth exemplary device 800 can be inserted within the through-hole in the tissue 30 employing the methods illustrated in FIGS. 2A-2D.

Figure 10B:
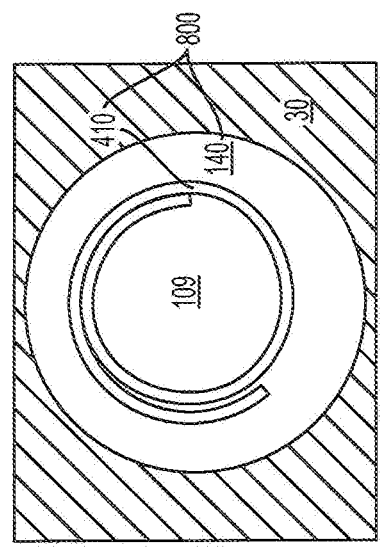
FIG. 10B is a vertical cross-sectional view of the eighth exemplary device after bioabsorption of the bioabsorbable tissue support and expansion of the non-bioabsorbable tissue support to enlarge the hole.

The spring-loaded non-bioabsorbable tissue support 410 is configured to expand during bioabsorption of the bioabsorbable tissue support 140 and to conform to a target shape upon release of stress in the elastic material. The target shape may, or may not, be a circular shape. After the insertion of the eighth exemplary device 800 in a through-hole of a tissue 30, the stress in the spring-loaded non-bioabsorbable tissue support 410 is gradually released during the bioabsorption of the bioabsorbable tissue support 140, which may take a time period ranging from 1 week to 8 weeks. FIG. 10B illustrates the configuration around the through-hole after the bioabsorbable tissue support 140 is absorbed into the tissue 30 and the spring-loaded non-bioabsorbable tissue support 410 is expanded to become a relaxed non-bioabsorbable tissue support 410' after relief of the stress built into the spring-loaded non-bioabsorbable tissue support 410. The through-hole in the tissue 30 may be enlarged during the process of the expansion of the spring-loaded non-bioabsorbable tissue support 410, and the expansion process stops when the spring-loaded non-bioabsorbable tissue support 410 becomes the relaxed non-bioabsorbable tissue support 410'.

Figure 11A:
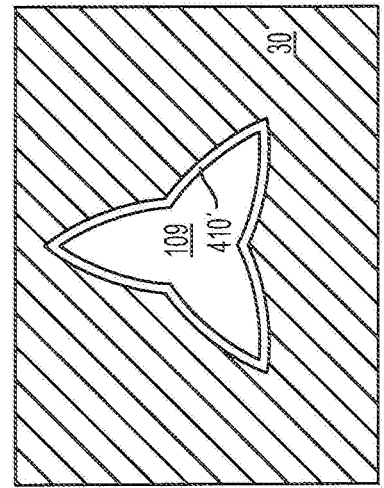
FIG. 11A is a vertical cross-sectional view of a ninth exemplary device employing a spring-loaded non-bioabsorbable tissue support embedded within a bioabsorbable tissue support as inserted within a hole in a tissue.
Figure 11B:
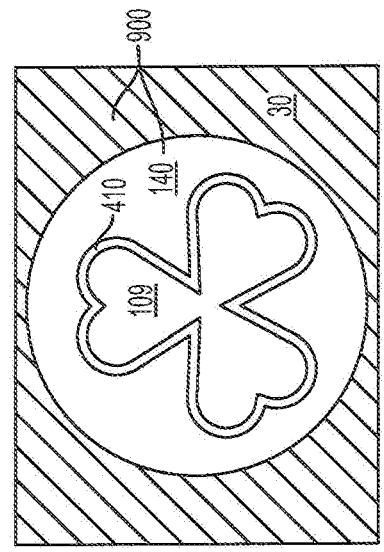
FIG. 11B is a vertical cross-sectional view of the ninth exemplary device portrayed in 11A after bioabsorption of the bioabsorbable tissue support and expansion of the non-bioabsorbable tissue support to enlarge and/or shape the hole.

Referring to FIG. 11A, a ninth exemplary device 900 of the present disclosure includes a spring-loaded non-bioabsorbable tissue support 410 embedded within a bioabsorbable tissue support 140 as in the eighth exemplary device 800. The ninth exemplary device 900 can be formed and installed in a through-hole in the same manner as the eighth exemplary device 800. The spring-loaded non-bioabsorbable tissue support 410 is self-expanding, and the expansive force of the spring-loaded non-bioabsorbable tissue support 410 is counterbalanced by the bioabsorbable tissue support 140 before the bioabsorbable tissue support 140 is absorbed by a tissue 30. The ninth exemplary device 900 can be derived from the eighth exemplary device by altering the shape and the energy of compression in the spring-loaded non-bioabsorbable tissue support 410 such that, upon relief of the stress in the spring-loaded non-bioabsorbable tissue support 410, the relaxed non-bioabsorbable tissue support 410' shown in FIG. 11B is at a target shape, which can be a non-circular shape.

Specifically, the spring-loaded non-bioabsorbable tissue support 410 is configured to expand during bioabsorption of the bioabsorbable tissue support 140 and to conform to a target shape upon release of stress in the elastic material. After the insertion of the eighth exemplary device 800 in a through-hole of a tissue 30, the stress in the spring-loaded non-bioabsorbable tissue support 410 is gradually released during the bioabsorption of the bioabsorbable tissue support 140, which may take a time period ranging from 1 week to 8 weeks. The spring-loaded non-bioabsorbable tissue support 410 gradually changes its shape during the bioabsorption of the at least one bioabsorbable material of the bioabsorbable tissue support 140.

During the shape change of the spring-loaded non-bioabsorbable tissue support 410, the spring-loaded non-bioabsorbable tissue support 410, still containing unrelieved stress, applies pressure at selective regions of sidewalls of the tissue 30 to prevent growth of new tissues therefrom while removing pressure at some other regions of the sidewalls of the tissue 30 to facilitate growth of new tissues therefrom. The growth of new tissues can be thus molded to induce formation of a target shape for the through-hole in the tissue, which can have peripheral surfaces of an arbitrary shape. The through-hole in the tissue 30 may be enlarged at selective regions during the process of the expansion of the spring-loaded non-bioabsorbable tissue support 410, and may shrink at other selective regions during the process of the expansion of the spring-loaded non-bioabsorbable tissue support 410. The molding process for the shape of the through-hole stops when the spring-loaded non-bioabsorbable tissue support 410 becomes the relaxed non-bioabsorbable tissue support 410'.

Referring to FIGS. 12A-12D, various types of tenth exemplary devices 1000 are shown. Each tenth exemplary device 1000 includes a non-bioabsorbable tissue support 310 and a bioabsorbable tissue support 140. An element configured to hang an attachment is affixed to an end surface of the non-bioabsorbable tissue support 310. The element configured to hang an attachment is herein referred to as a "hanging structure."

For example, if the non-bioabsorbable tissue support 310 includes an end plate, the hanging structure (420, 430, 440, or 450) can be affixed to the outer surface of the end plate. If an end plate is not provided, the hanging structure (420, 430, 440, or 450) can be affixed to a sidewall surface of an elongated portion of the non-bioabsorbable tissue support 310 that is located on the opposite side of a pointed tip portion of the bioabsorbable tissue support 140. In one embodiment, the hanging structure (420, 430, 440, or 450) can be of integral construction with the non-bioabsorbable tissue support 310. For example, the hanging structure (420, 430, 440, or 450) can be welded to the non-bioabsorbable tissue support 310, or the combination of the hanging structure (420, 430, 440, or 450) and the non-bioabsorbable tissue support 310 can be molded as a single contiguous piece, i.e., as an integral structure.

Figure 12A:
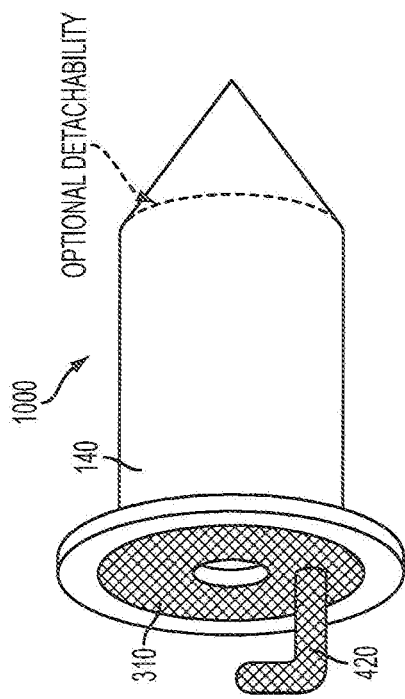
FIG. 12A is an angled view of a first type of tenth exemplary device including a non-bioabsorbable tissue support containing a hook, and a bioabsorbable tissue support. This is an example of the device with an endplate for attachment of an ornamental device while the bioabsorbable tissue support is promoting healing.
Figure 12B:
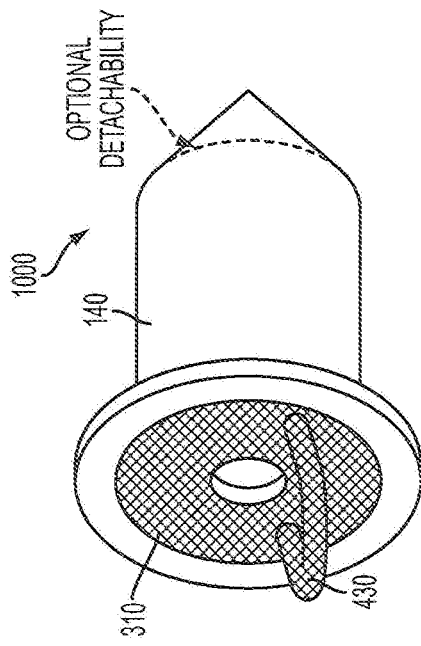
FIG. 12B is an angled view of a second type of the tenth exemplar device including a non-bioabsorbable tissue support containing a hoop for hanging a hook, and a bioabsorbable tissue support.
Figure 12C:
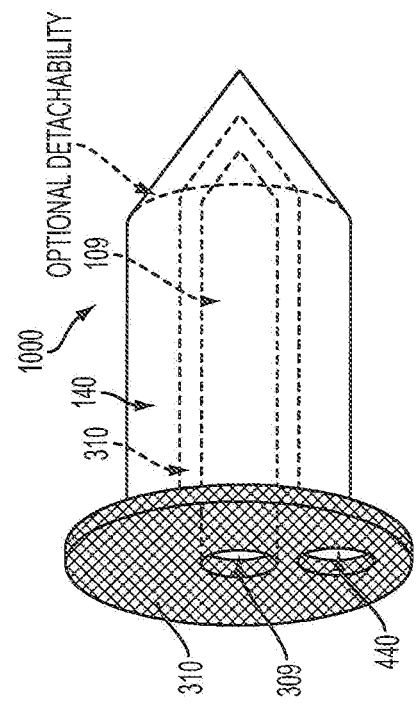
FIG. 12C is an angled view of a third type of the tenth exemplar device including a non-bioabsorbable tissue support containing a hole in a plate, and a bioabsorbable tissue support.
Figure 12D:
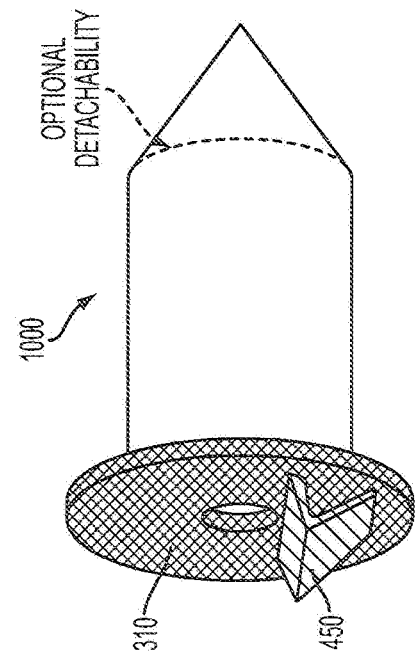
FIG. 12D is an angled view of a fourth type of the tenth exemplary device including a non-bioabsorbable tissue support containing an elastic clip, and a bioabsorbable tissue support.

In one embodiment, the non-bioabsorbable tissue structure 310 includes a sidewall surface including an opening connected to a cavity 109 within the non-bioabsorbable tissue structure 310. The hanging structure (420, 430, 440, or 450) is affixed to an end of the sidewall surface including the opening. The hanging structure (420, 430, 440, or 450) may be selected from a hook 420 as illustrated in FIG. 12A, a hoop 430 for hanging a hook as illustrated in FIG. 12B, a hole 430 in a plate that is a portion of the non-bioabsorbable tissue structure 310 as illustrated in FIG. 12C, and an elastic clip 450 as illustrated in FIG. 12D.

Figure 13A:
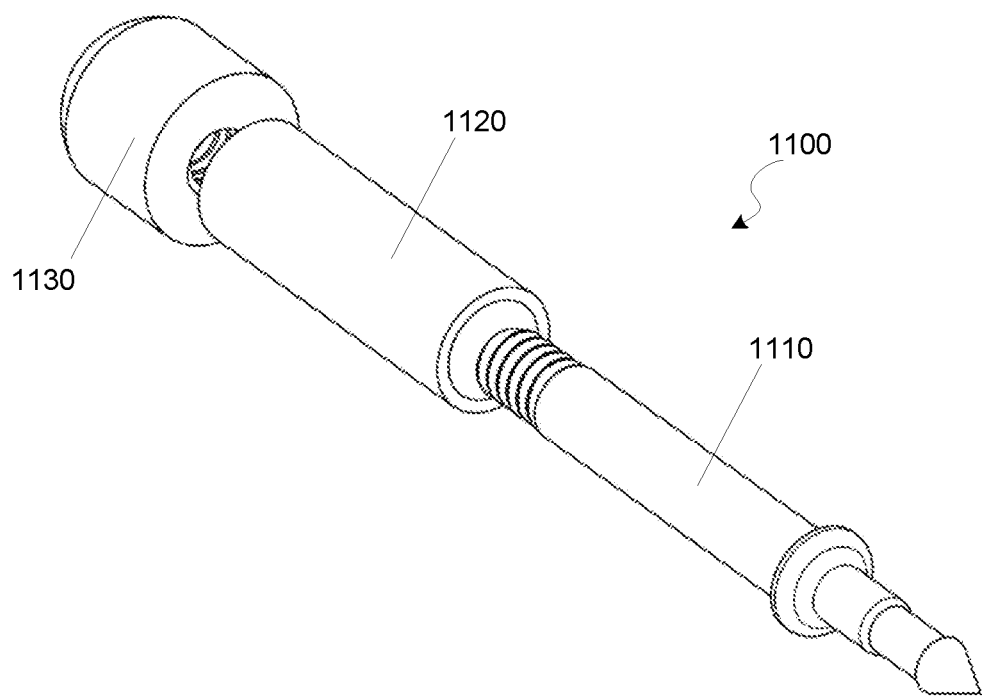
FIG. 13A is an angled view of the eleventh exemplary device including a sleeve, a stud, and a nut.
Figure 13B:
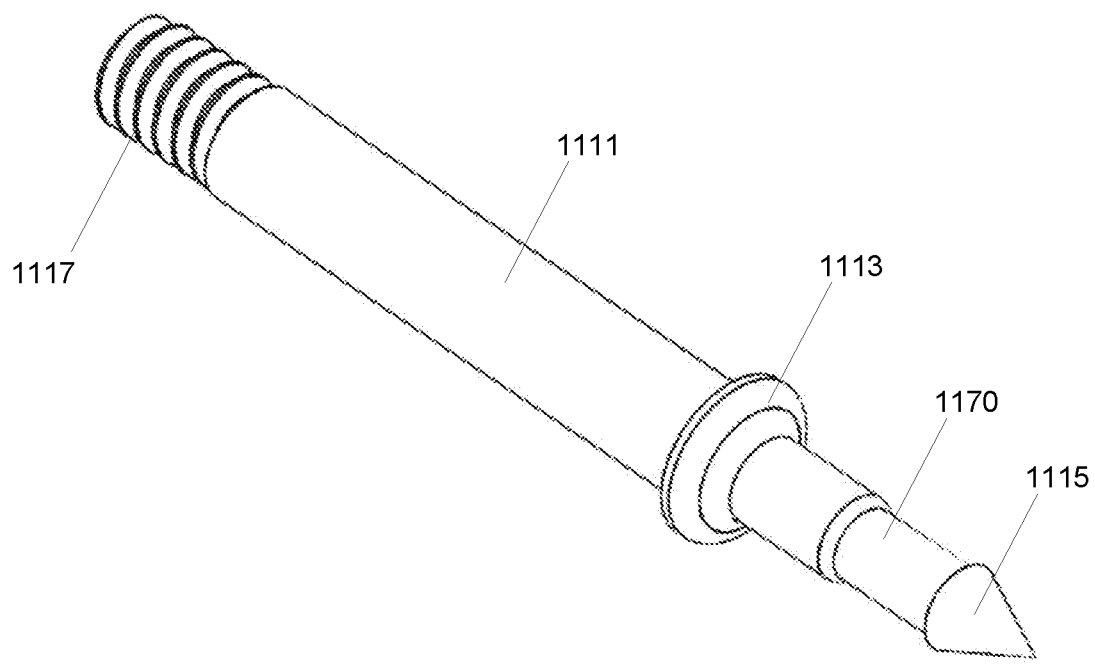
FIG. 13B is an angled view of the stud of FIG. 13A.

Referring to FIGS. 13A and 13B, an eleventh exemplary device 1100 is shown. Device 1100 comprises a sleeve 1120 that is made from a bioabsorbable material as described herein, preferably with a therapeutic compound or dye dispersed in the bioabsorbable material. The sleeve 1120 is hollow and a stud 1110 is removably inserted into the hollow sleeve 1120 when piercing tissue. Exemplary device 1100 is compatible with existing piercing guns for inserting the device 1100 into tissue.

The stud 1110 has a pointed tip 1115 on one end, and a flange 1113 near the opposite end and spaced apart from the pointed tip 1115. When the stud 1110 is inserted into the sleeve 1120, the flange abuts against the sleeve 1120, leaving the pointed tip 1115 exposed while rod portion 1111 remains within the sleeve. In some embodiments, the flange 1113 is shaped as a disc. In other embodiments, the flange 1113 is a tapered sleeve holder that conical or longitudinally tapered along a longitudinal axis of the stud. Device 1100 also has a removable nut 1130 that attaches to the opposite end of the stud from the pointed tip 1115. In one embodiment, the nut and the stud has complementary threading 1117 for threaded attachment. In other embodiments, the nut and the stud are attached by snap fit or pressure fit. Since the nut 1130 is larger than the hollow cavity of the sleeve 1120, when the stud 1113 is inserted into the sleeve 1120 for piercing and the nut 1130 attached, this configuration prevents the stud 1113 from being pulled out of sleeve 1120 since the sleeve is clamped between the flange and the nut. After piercing, the nut 1130 and the stud 1110 are removed, leaving only the sleeve 1120 in the pierced tissue for gradual release of the therapeutic or dye compounds.

In alternate embodiments, the pointed tip 1115 is also removable and attached to the stud 1110 by threading, snap fit, or pressure fit. In this alternate embodiment, after piercing the nut 1130 and the pointed tip 1115 are removed, leaving the sleeve 1120 and the rod portion 1111 of the stud (inside the sleeve) in the pierced tissue. In some embodiments, once the nut and the pointed tip are removed, the two ends of the rod potion 1111 are then available for attachment to an earring or an identification device, such as by threading, snap fit, or pressure fit.

In one embodiment, the stud has a neck potion 1170 between the flange 1113 and the pointed tip 1115 for attachment to a clamping device.

In some embodiments, the stud and the nut is made of a resin material. Example resins include, but are not limited, to plant based resins or synthetic resins. In one embodiment, the stud is made of a photosensitive resin, preferably a UV sensitive resin. Example UV sensitive resins include, but are not limited to: Thiol-ene-based photocurable resins: trimethylolpropane tris(3-mercaptopropionate) (TMPMP), pentaerythritol tetra(3-mercaptopropionate) (PETMP), tris[2-(3-mercaptopropionyloxy) ethyl] isocyanurate (TMI), or pentaerythritol tetrakis (3-mercaptopropionate) (PE-1). Photosensitive resins allow for manufacturing the stud by 3D printing, thereby allowing the stud to be made with various cross-sectional shapes. For example, the stud can be made to have a longitudinally tapered profile, a polygonal cross-sectional shape, or a rounded cross-sectional shape. Where the stud has a cross-sectional shape, the stud (made of resin which is more rigid than the bioabsorbable material) when inserted in the sleeve (made of a softer bioabsorbable material) reinforces the sleeve into the cross-sectional shape of the stud or another shape.

In some embodiments, the sleeve is made from a photopolymer. Example photopolymers include, but are not limited to: (Meth)acrylate-based resins: PEGDA, UDMA, triethylene glycol dimethacrylate (TEGDMA), bisphenol A-glycidyl methacrylate (Bis-GMA), trimethylolpropane triacrylate (TTA), or bisphenol A ethoxylate diacrylate (Bis-EDA). Photopolymers allow for manufacturing the sleeve by 3D printing, in turn allowing the sleeve to be made with various cross-sectional shapes. In some embodiments, the sleeve is multilayered. In one embodiment, each layer of the sleeve is made of a different bioabsorbable material or polymer. In one embodiment, each layer of the sleeve has a different therapeutic or dye compound. In some embodiments, the thickness of the sleeve is between 10 micro meter to 1000 micro meter. In one embodiment, the sleeve is about 10 micro meter, 50 micro meter, 100 micro meter, 250 micro meter, 500 micro meter, 750 micro meter, or 1000 micro meter in thickness.

The various devices of the present disclosure can be employed to form custom-tailored shape for the through-hole for attaching an attachment, which can be, for example, body-piercing items that may be decorative, therapeutic, and/or administrative (such as identification of animals). The size of the through-hole may be controllable by adjusting the inflation of a balloon employed to expand an expandable device of the present disclosure, or by setting the spring parameters of the self-expanding spring-loaded devices of the present disclosure. The various chemicals that are absorbed during the bioabsorption of the bioabsorbable materials can provide ornamental, therapeutic, and/or anesthetic purposes. The progress of the healing process may be monitored by use of a dye among the at least one bioabsorbable materials. The therapeutic function of the devices of the present disclosure may be customized depending on the species for which the devices are employed.

While the invention has been described in terms of specific embodiments, it is evident in view of the foregoing description that numerous alternatives, modifications and variations will be apparent to those skilled in the art. Each of the various embodiments of the present disclosure can be implemented alone, or in combination with any other embodiments of the present disclosure unless expressly disclosed otherwise or otherwise impossible as would be known to one of ordinary skill in the art. Accordingly, the invention is intended to encompass all such alternatives, modifications and variations which fall within the scope and spirit of the invention and the following claims.

The invention claimed is:

1. A device for support of a puncture in a tissue, said device comprising:
   a bioabsorbable tissue support comprising:
      an tubular elongated sleeve having a cross-sectional shape and a thickness defined between an inner surface and an outer surface of the tubular elongated sleeve, wherein the tubular elongated sleeve is configured to contact an inner surface of said puncture; and
      a cavity extending through said elongated sleeve for receiving an earring or an identification device;
   wherein the tubular elongated sleeve is uniformly made from at least one bioabsorbable material throughout the entire thickness of the tubular elongated sleeve, the bioabsorbable material comprising a polymer;
   wherein the tubular elongated sleeve is configured to extend through the tissue and remains after said at least one bioabsorbable material is absorbed through at least a skin of a subject; and
   wherein one or more of said at least one bioabsorbable material comprises a functional compound mixed within the polymer for absorption through the skin as the bioabsorbable material is absorbed, the functional compound selected from a group consisting of therapeutic medical chemicals, anesthetic materials, dye materials, and antiproliferative agents.

2. The device of claim 1, wherein the identification device is an RFID tag.

3. The device of claim 1, wherein the bioabsorbable tissue support comprises a removable stud, wherein the stud comprises:
   a rod portion for insertion into the cavity, the rod having a first end and a second end;
   the pointed tip disposed at the first end of the rod portion, such that the bioabsorbable tissue support is configured to pierce through the tissue for creating the puncture; and
   a flange proximate to the first end and configured to abut against a first end of the tubular elongated sleeve when the stud is inserted into the cavity, thereby keeping the pointed tip exposed out of the tubular elongated sleeve.

4. The device of claim 3, wherein the bioabsorbable tissue support comprises a capping nut configured to removably attach to a second end of the rod portion of the stud, wherein the capping nut has a cross-section that is greater than the cavity, such that when the stud is inserted into the cavity and the capping nut is attached to the second end of the rod portion, the tubular elongated sleeve is secured between the capping nut and the flange potion.

5. The device of claim 4, wherein the capping nut is removably attachable to the second end of the rod portion of the stud by threading, snap fit, or pressure fit.

6. The device of claim 4, wherein the stud and the capping nut is made of a resin.

7. The device of claim 6, wherein the resin is an UV sensitive resin, and the stud is manufactured by 3D printing.

8. The device of claim 3, wherein the pointed tip is removably attached to the second end of the rod portion of the stud by threading, snap fit, or pressure fit.

9. The device of claim 8, wherein one or both of the first end and the second end of the rod is configured for removable attachment to the earring or the identification device.

10. The device of claim 1, wherein the polymer comprises a poly-lactic-co-glycolic acid (PLGA) polymer matrix.

11. The device of claim 10, wherein the PLGA polymer matrix has a lactic to glycolic ratio of between 15:85 to 85:15.

12. The device of claim 11, wherein the PLGA polymer matrix has a molecular weight of greater than 100 kDa.

13. The device of claim 1, wherein the tubular elongated sleeve comprises one or more layers having:
   a first layer comprising a first bioabsorbable material providing a first functionality selected from therapeutic treatment of said puncture, anesthetic treatment of said puncture, coloring of a region around said puncture, and prevention of change of shape of said puncture.

14. The device of claim 13, wherein the first bioabsorbable material comprises a photopolymer, and the outer layer is manufactured by 3D printing.

15. The device of claim 13, wherein the stud has a first cross-sectional shape, and wherein the stud has a higher rigidity than the tubular elongated sleeve thereby reinforcing a second cross-sectional shape of the tubular elongated sleeve.

16. The device of claim 13, wherein the tubular elongated sleeve comprises a second layer comprising a second bioabsorbable material providing a second functionality selected from therapeutic treatment of said puncture, anesthetic treatment of said puncture, coloring of a region around said puncture, and prevention of change of shape of said puncture, said second functionality being different from said first functionality.

17. The device of claim 16, wherein the first bioabsorbable material has a first absorption half-life, and the second bioabsorbable material has a second bioabsorption half-life that is longer than said first bioabsorption half-life.

18. The device of claim 1, wherein the functional compound is microencapsulated.

19. The device of claim 1, wherein the elongated sleeve has a tubular mesh structure with openings therein.

20. The device of claim 1, further comprising an expansion-inducing device embedded within a cavity in said elongated sleeve.

21. The device of claim 20, wherein the non-bioabsorbable tissue support includes an elastic material that is spring loaded in a compressed state by said bioabsorbable tissue support, and is configured to expand during bioabsorption of said bioabsorbable tissue support and to conform to a target shape upon release of stress in said elastic material.

22. The device of claim 20, wherein the expansion-inducing device is a balloon, a spring, or a coil.

23. The device of claim 1, wherein the bioabsorbable tissue support includes:
   a bioabsorbable dye; and
   at least one material selected from the group consisting of therapeutic medical chemicals, anesthetic materials, and antiproliferative agents.

24. The device of claim 1, wherein the thickness of the tubular elongated sleeve is between 10 micro meter to 1000 micro meter.

* * * * *